US010597425B2

(12) United States Patent
Pfeilsticker et al.

(10) Patent No.: US 10,597,425 B2
(45) Date of Patent: Mar. 24, 2020

(54) ANTI-GP41 ANTIBODY-SPECIFIC CAPTURE AGENTS, COMPOSITIONS, AND METHODS OF USING AND MAKING

(71) Applicant: California Institute of Technology, Pasadena, CA (US)

(72) Inventors: Jessica A. Pfeilsticker, Pasadena, CA (US); Aiko Umeda, North Hollywood, CA (US); James R. Heath, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/484,610

(22) Filed: Sep. 12, 2014

(65) Prior Publication Data

US 2015/0099658 A1 Apr. 9, 2015

Related U.S. Application Data

(60) Provisional application No. 61/877,112, filed on Sep. 12, 2013.

(51) Int. Cl.

*C07K 9/00* (2006.01)
*C07K 7/08* (2006.01)
*G01N 33/569* (2006.01)

(52) U.S. Cl.

CPC .................. *C07K 9/00* (2013.01); *C07K 7/08* (2013.01); *G01N 33/56988* (2013.01); *G01N 2333/162* (2013.01); *G01N 2469/20* (2013.01)

(58) Field of Classification Search

None

See application file for complete search history.

(56) References Cited

U.S. PATENT DOCUMENTS

2012/0202219 A1 8/2012 Agnew et al.

FOREIGN PATENT DOCUMENTS

WO WO 2012/106671 9/2012
WO WO 2013/033561 3/2013
WO WO 2013/074907 5/2013
WO WO 2013/009869 12/2013

OTHER PUBLICATIONS

Manea et al., J. Med. Chem., 2008, 51:1150-1161.*

International Search Report and Written Opinion, PCT/US2014/055414, filed Sep. 12, 2014, dated Dec. 17, 2014.

Millward et al., 'Iterative in situ click chemistry assembles a branched capture agent and allosteric inhibitor for Akt1', Journal of the American Chemical Society. vol. 133, No. 45, pp. 18280-18288 (2011).

Millward et al., 'In situ click chemistry: from small molecule discovery to synthetic antibodies' Integrative Biology, vol. 5, No. 1, pp. 87-95 (Jan. 2013).

Mamidyala et al., 'In situ click chemistry: probing the binding landscapes of biological molecules' Chemical Society Reviews, vol. 39, No. 4, pp. 1252-1261 (2010).

Bianchi et al., 'Vaccination with peptide mimetics of the gp41 prehairpin fusion intermediate yields neutralizing antisera against HIV-1 isolates' PNAS, vol. 107, No. 23. pp. 10655-10660 (2010).

Pfeilsticker et al., 'A cocktail of thermally stable, chemically synthesized capture agents for the efficient detection of anti-gp41 antibodies from human sera' PloS One, vol. 8, Issue No. 10. Article No. e76224 (internal pp. 1-5) (e-pub. Oct. 7, 2013).

* cited by examiner

*Primary Examiner* — Nicole Kinsey White

(74) *Attorney, Agent, or Firm* — Pabst Patent Group LLP

(57) ABSTRACT

The present application provides stable peptide-based anti-gp41 antibody capture agents and methods of use as detection and diagnosis agents. The application further provides methods of manufacturing anti-gp41 antibody capture agents using iterative on-bead in situ click chemistry.

26 Claims, 9 Drawing Sheets

Specification includes a Sequence Listing.

(i)

Biotin-$PEG_5$-IWCGSGKLICTTA(SEQ ID NO: 1)-Pra-($T_z$-$Az_4$-nidnG(SEQ ID NO: 2)-$CONH_2$)-$CONH_2$ (ii)

C-terminus

Biotin-$PEG_5$-IWCGSGKLICTTA(SEQ ID NO: 1)-Pra-($T_z$-$Az_4$-hnpfk(SEQ ID NO:3)-$CONH_2$)-$CONH_2$ (iii)

C-terminus

Biotin-PEG5-IWCGSGK(SEQ ID NO: 27)-Pra-(Tz-Az4-eihny(SEQ ID NO:4)-CONH2)-ICTTA(SEQ ID NO: 5)-CONH2

SEQUENCE LISTING

```
<160> NUMBER OF SEQ ID NOS: 27

<210> SEQ ID NO 1
<211> LENGTH: 13
<212> TYPE: PRT
<213> ORGANISM: Artificial Sequence
<220> FEATURE:
```

-continued

```
<223> OTHER INFORMATION: Synthetic Peptide

<400> SEQUENCE: 1

Ile Trp Cys Gly Ser Gly Lys Leu Ile Cys Thr Thr Ala
1               5                   10


<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 2

Asn Ile Asp Asn Gly
1               5


<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 3

His Asn Pro Phe Lys
1               5


<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 4

Glu Ile His Asn Tyr
1               5


<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 5

Ile Cys Thr Thr Ala
1               5


<210> SEQ ID NO 6
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 6

Ser Gly Lys Leu Ile Cys
1               5


<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide
```

<400> SEQUENCE: 7

Ser Gly Lys Leu Ile Cys Thr Thr Ala
1 5

<210> SEQ ID NO 8
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 8

Asp Lys Gly Leu Pro
1 5

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 9

Val Ala Asp Pro Ala
1 5

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 10

Pro Gly Val Thr Phe
1 5

<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 11

Ser Arg Arg Arg Ser
1 5

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa is Gln or Glu

<400> SEQUENCE: 12

Asp Xaa Gly Ala Phe
1 5

<210> SEQ ID NO 13
<211> LENGTH: 5
<212> TYPE: PRT

<213> ORGANISM: Artificial Sequence
<220> FEATURE:
<223> OTHER INFORMATION: Synthetic Peptide

<400> SEQUENCE: 13

Tyr Trp Asp Tyr Asn
1 5

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 14

His Leu Leu Tyr Gln
1 5

<210> SEQ ID NO 15
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 15

Ser Gly Ala Gln Ser
1 5

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 16

Asp Asp Trp Ala Ile
1 5

<210> SEQ ID NO 17
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 17

Gln Ile Asp Leu Arg
1 5

<210> SEQ ID NO 18
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 18

Thr Phe Leu Gln Ser
1 5

<210> SEQ ID NO 19
<211> LENGTH: 5
<212> TYPE: PRT
<213> ORGANISM: Artificial Sequence -continued
<220> FEATURE:
<223> OTHER INFORMATION: Synthetic Peptide

<400> SEQUENCE: 19

Trp Gly Glu His Pro
1 5

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 20

Gln Asn Asp Trp Lys
1 5

<210> SEQ ID NO 21
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 21

Leu Thr Ser Arg Tyr
1 5

<210> SEQ ID NO 22
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 22

Asp Ile Lys Ser Pro
1 5

<210> SEQ ID NO 23
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 23

Gln Pro Ile Asp Gln
1 5

<210> SEQ ID NO 24
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 24

Lys Ile Asp Arg Tyr
1 5

-continued

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa is Pro or Asp

<400> SEQUENCE: 25

Gln Ser Xaa Trp Leu
1 5

<210> SEQ ID NO 26
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 26

Glu Gln Thr Phe Asp
1 5

<210> SEQ ID NO 27
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 27

Ile Trp Cys Gly Ser Gly Lys
1 5

ANTI-GP41 ANTIBODY-SPECIFIC CAPTURE AGENTS, COMPOSITIONS, AND METHODS OF USING AND MAKING

RELATED APPLICATIONS

This application claims priority from U.S. Provisional Patent Application No. 61/877,112, filed on Sep. 12, 2013, incorporated by reference herein in its entirety.

STATEMENT REGARDING FEDERALLY SPONSORED RESEARCH OR DEVELOPMENT

This invention was made with government support under Grant No. W911NF-09-D-0001 awarded by the U.S. Army. The government has certain rights in the invention.

BACKGROUND

The early detection of viruses including the Human Immunodeficiency Virus (HIV) requires multiplex detection of anti-glycoprotein 41 (gp41) antibodies in biological samples. The availability of high-affinity, highly selective molecular moieties that recognize anti-gp41 antibodies from complex biological mixtures is a critical component for accurate detection of anti-gp41 antibodies that may indicate HIV infections.

Detecting the immune response to an infectious agent can provide a useful in vitro diagnostic surrogate relative to direct pathogen detection. Such assays are commonly used for detecting HIV infection because of HIV's characteristic immunopathology. However, direct detection of HIV viral RNA and p24 antigen is only effective at an early stage of infection, approximately 2-6 weeks of initial exposure. Antibodies against HIV envelope proteins emerge in patients' blood around 3-4 weeks of infection as the viral RNA and p24 levels decline as a result of immunocomplex formation. The high serum level of anti-HIV IgG is maintained throughout the course of clinical latency (2-20+ years), during which time viral antigens are under detection limits until the onset of acquired immunodeficiency syndrome (AIDS). Viral load and $CD4^+$cell counts are mainly used for prognostic purposes to monitor the efficacy of treatments; however viral load is sometimes used for the diagnosis of infant HIV infections where antibody-based assays are not applicable. Assays for anti-HIV antibodies are the most widely used diagnostic test both in cases where infection is presumed to have occurred more than 6 weeks prior to testing, and for epidemiological reasons, to estimate the incidence of HIV in a population, since, with the exception of infant HIV, virtually 100% of the infected individuals express these antibodies. Typically in these assays, immunogenic and conserved antigens from the HIV are expressed as regions of a single chimeric protein. That chimeric protein is then used to capture specific antibodies from the body fluid (e.g. blood, saliva or urine) of potentially infected patients; a positive assay result implies infection. However, the polyclonal diversity of antibodies across a patient population can translate into large variations in assay performance from patient to patient. In addition, the chimeric recombinant proteins are biological reagents, and so may have limitations related to shelf life and batch-to-batch variability. These limitations can adversely influence the performance of a diagnostic test, especially one that is deployed in harsh physical environments. Accordingly, there remains a need for new compositions and assays for the diagnosis of HIV.

SUMMARY

The present disclosure relates to chemically synthesized capture agents (called protein-catalyzed capture agents, or PCC Agents) that are designed to sample the polyclonal diversity of an antibody-based immune response, methods for making said capture agents using iterative in situ click chemistry, methods for using said capture agents to detect anti-glycoprotein 41 (gp41) antibodies, and assays employing said methods. The performance of such an assay is compared to the gold standard chimeric protein antigen using sera collected from a cohort of HIV-1-positive human subjects, plus controls. The present disclosure also describes favorable thermal stability of compositions comprising one or more capture agents. Thermal stability is relevant to point-of-care HIV diagnostic assays, for example, in locations that lack refrigeration.

In one aspect, provided herein is a stable, synthetic capture agent that specifically binds an anti-gp41 antibody, wherein the capture agent comprises a designed anchor ligand, a designed secondary ligand, optionally a designed tertiary ligand, and optionally a designed quarternary ligand, and wherein the ligand selectively binds an anti-gp41 antibody. In one embodiment, the capture agent binds to residues 600-612 (IWCGSGKLICTTA) (SEQ ID NO: 1) of gp41. In another embodiment, the binding of the capture agent to an anti-gp41 antibody indicates the presence of HIV.

In another aspect, provided herein is a composition comprising one or more synthetic capture agents, as described herein, that specifically bind an anti-gp41 antibody.

In another aspect, provided herein is a method for detecting anti-gp41 antibodies in a biological sample, comprising the step of treating the biological sample with one or more capture agents of the invention.

In another aspect, provided herein is method of diagnosing an HIV infection in a subject, the method comprising the steps of: a) administering to the subject one or more capture agents of the invention, wherein each capture agent is linked to a detectable moiety; and b) detecting the moiety linked to each capture agent; wherein detection of the moiety diagnoses an HIV infection in the subject.

Anchor Ligand

In one embodiment of the capture agent, the anchor ligand comprises a chemically modified variant of a conserved, immunogenic epitope on the HIV-1 gp41 protein. In another embodiment, the epitope on the HIV-1 gp41 protein corresponds to residues 600-612 (IWCGSGKLICTTA) (SEQ ID NO: 1) of gp41. In certain embodiments, the anchor ligand comprises an amino acid sequence that is 80 to100% identical to residues 600-612 (IWCGSGKLICTTA) (SEQ ID NO: 1) of gp41. In some embodiments, the anchor ligand is chemically modified to comprise a detection lable (e.g., biotin, biotin PEG, DOTA, NOTA, and the like).

Secondary Ligand

The secondary ligand is selected via an in situ click screen from a large (e.g., $10^6$ element) one-bead-one-compound (OBOC) peptide library. In some embodiments, the secondary ligand consists of 5 amino acids. In one embodiment, the peptide library is comprehensive for 5-mers, with a $6^{th}$ amino acid at the N-terminus presenting azide functionality. In one embodiment, the library comprises non-natural (D) stereoisomers of the 20 natural amino acids, excluding cysteine and methionine.

In some embodiments, the secondary ligand is selected from the ligands of Table 1. In a particular embodiment, the secondary ligand comprises the sequence nidnG (SEQ ID NO: 2). In another particular embodiment, the secondary ligand is hnpfk (SEQ ID NO: 3). In another particular embodiment, the secondary ligand is eihny (SEQ ID NO: 4).

In another particular embodiment, the secondary ligand comprises the sequence Az4-nidnG(SEQ ID NO: 2)-$CONH_2$. In another particular embodiment, the secondary ligand comprises the sequence Az4-hnpfk(SEQ ID NO: 3)-$CONH_2$. In another particular embodiment, the secondary ligand comprises the sequence Az4-eihny(SEQ ID NO: 4)-$CONH_2$.

In another particular embodiment, the secondary ligands correspond to the sequences disclosed in Table 1 and FIG. 1.

Tertiary and Quaternary Ligands

The tertiary and quaternary ligands, if present, are selected via an in situ click screen from a large (e.g., $10^6$ element) one-bead-one-compound (OBOC) peptide library.

Triazole Linkage

In one embodiment of the capture agent, the anchor ligand and secondary ligand are linked together via a 1,4-substituted-1,2,3-triazole residue (Tz4). In another embodiment, the secondary ligand and the tertiary ligand are linked together via a 1,4-substituted-1,2,3-triazole residue (Tz4). In yet another embodiment, the tertiary ligand and the quarternary ligand are linked together via a 1,4-substituted-1,2,3-triazole residue (Tz4). In yet another embodiment, the anchor ligand and secondary ligand are linked together via a 1,4-substituted-1,2,3-triazole residue, and the secondary ligand and the tertiary ligand are linked together via a 1,4-substituted-1,2,3-triazole residue. In yet another embodiment, the anchor ligand and secondary ligand are linked together via a 1,4-substituted-1,2,3-triazole residue, the secondary ligand and the tertiary ligand are linked together via a 1,4-substituted-1,2,3-triazole residue and the tertiary ligand and the quarternary ligand are linked together via a 1,4-substituted-1,2,3-triazole residue.

Bilagands, Triligands and Tetraligands

In certain embodiments, the anti-gp41 antibody capture agent has a structure selected from the structures shown in FIG. 1. Acetylene-presenting anchor peptides (black) were derived from the immunogenic epitope of HIV-1 gp41 (residues 600-612). A21-nidnG (SEQ ID NO: 2) (i) and A21-hnpfk (SEQ ID NO: 3) (ii) were evolved from the original epitope appended with Pra at the C-terminus whereas A22-eihny (SEQ ID NO: 4) (iii) utilized the "substituted" anchor wherein residue Leu-607 was replaced with Pra. Secondary ligand branches were identified from the in situ click screen of a 5-mer OBOC library presenting azide functionality. Biligands (i) and (ii) were raised against the target anti-HIV antibody 3D6, and the biligand (iii) was raised against the antibody 4B3.

In one embodiment, the capture agent is a biligand. In another embodiment, the capture agent is a triligand. In still another embodiment, the capture agent is a tetraligand.

In one embodiment, the capture agent binds to anti-HIV antibody 3D6. In another embodiment, the capture agent binds to anti-HIV antibody 4B3.

Properties

In certain embodiments, the anti-gp41 antibody capture agents provided herein are stable across a wide range of temperatures, pH's, storage times, storage conditions, and reaction conditions, and in certain embodiments the capture agents are more stable than a comparable antibody or biologic. In certain embodiments, the capture agents are stable in storage as a lyophilized powder. In certain embodiment, the capture agents are stable in storage at a temperature of about −80° C. to about 60° C. In certain embodiments, the capture agents are stable at room temperature. In certain embodiments, the capture agents are stable in human serum for at least 24 hours. In certain embodiments, the capture agents are stable at a pH in the range of about 3 to about 12. In certain embodiments, the capture agents are stable as a powder for two months at a temperature of about 60° C.

Detectable Labels

In some embodiments, the capture agent is labeled with a label selected from the group consisting of biotin, copper-DOTA, biotin-PEG3, aminooxyacetate, $^{19}$FB, $^{18}$FB and FITC-PEG3. In other embodiments, the capture agent is labeled with the detectable moiety consisting of $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C and $^{76}$Br. In other embodiments, the label is a fluorescent label. In a particular embodiment, the detectable label is $^{18}$F.

Methods and Uses

As used herein, the terms "capture agent of the invention", or "capture agents of the invention" refer to synthetic protein-catalyzed capture agents which bind anti-gp41 antibodies, as described herein.

Provided is a method of diagnosing an HIV infection in a subject, the method comprising the steps of: a) administering to a biological sample from the subject a capture agent of the invention, wherein the capture agent is linked to a detectable moiety; and b) detecting the moiety linked to the capture agent; wherein detection of the moiety diagnoses an HIV infection in the subject. Also provided is the use of one or more capture agents of the invention for the diagnosis of an HIV infection in a subject.

Also provided is a method of detecting an anti-gp41-antibody in a subject, comprising the step of contacting a biological sample from the subject with one or more capture agents of the invention. Also provided is the use of one or more capture agents of the invention for the detection of an anti-gp41-antibody in a subject.

Also provided is a method of detecting anti-gp41 antibodies in a biological sample using an immunoassay, wherein the immunoassay utilizes a capture agent as described herein, and wherein said capture agent replaces an antibody or its equivalent in the immunoassay. In certain embodiments, methods are provided for identifying, detecting, quantifying, or separating anti-gp41 antibodies in a biological sample using the capture agents as described herein. In one embodiment of the method, the immunoassay is selected from the group of Western blot, pull-down assay, dot blot, and ELISA.

Also provided is a method of detecting the presence of anti-gp41 antibodies in a human or mammalian subject, the method comprising the steps of:

a) administering to a biological sample from the subject one or more capture agents of the invention, wherein each capture agent is linked to a detectable moiety; and b) detecting the moiety linked to each capture agent in the subject; wherein detection of the moiety indicates the presence of anti-gp41 antibodies in the subject.

Also provided herein is a method of detecting anti-gp41 antibodies in a sample comprising:

a) exposing the sample to one ore more capture agents of the invention, wherein each capture agent is linked to a detectable moiety;

b) binding antibody in the biological sample to a substrate and b) detecting the moiety linked to each capture agent on the substrate; wherein detection of the moiety on the substrate detects anti-gp41 antibodies in the sample.

Also provided is a method of monitoring treatment of a subject receiving HIV-directed therapy comprising administering to a first biological sample from the subject one or more capture agents described above, wherein each capture agent is linked to a detectable moiety; detecting the moiety linked to the capture agent bound to an anti-gp41 antibody; administering a treatment for HIV to the subject; administering to a second biological sample from the subject one or more capture agents described above, wherein each capture agent is linked to a detectable moiety; and detecting the moiety linked to the capture agent bound to an anti-gp41 antibody, wherein if less of the moiety is detected on the substrate in step d) than in step b) the treatment is improving the HIV infection in the subject.

Kits

Provided herein in certain embodiments are kits comprising one or more capture agents of the invention. In certain embodiments, these kits may be used for identifying, detecting, quantifying, and/or separating anti-gp41 antibodies, and in certain embodiments the kits may be used in the diagnosis and/or staging of a conditions associated with the presence of anti-gp41 antibodies. In certain embodiments, a kit as provided herein comprises: (a) a substrate comprising an adsorbent thereon, wherein the adsorbent is suitable for binding anti-gp41 antibodies, and (b) a washing solution or instructions for making a washing solution, wherein the combination of the adsorbent and the washing solution allows detection of anti-gp41 antibodies. In other embodiments, the kits provided herein may be used in the treatment of a condition associated with the presence of anti-gp41 antibodies.

In certain embodiments, a kit may further comprise instructions for suitable operational parameters in the form of a label or a separate insert. For example, the kit may have standard instructions informing a consumer/kit user how to wash the probe after a sample of plasma or other tissue sample is contacted on the probe.

In certain embodiments, a kit as comprises (a) one or more capture agents that specifically bind anti-gp41 antibodies; and (b) a detection reagent. Such kits can be prepared from the materials described herein.

The kits provided herein may optionally comprise a standard or control information, and/or a control amount of material, so that the test sample can be compared with the control information standard and/or control amount to determine if the test amount of anti-gp41 antibodies detected in a sample is an amount consistent with a diagnosis of a particular condition.

Synthesis of Capture Agents

Provided herein are methods for making (i.e., synthesizing) the anti-gp41 antibody capture agents of the invention. In one embodiment, the method comprises the steps of:

(a) providing an anchor ligand;

(b) identifying a secondary ligand by the following steps:

(i) preparing an anchor ligand selection block comprising the anchor ligand and an azido group or an alkynyl group;

(ii) preparing a plurality of candidate peptides to select a secondary ligand for the target protein, the plurality of peptides comprising an azido group, or an alkynyl group, if the anchor ligand selection block comprises an alkynyl group, or an azido group, respectively;

(iii) contacting the anchor ligand selection block and the plurality of peptides with the target protein (e.g., an anti-gp41 antibody);

(iv) providing a capture agent biligand by forming a disubstituted 1,2,3-triazole linkage between the anchor ligand selection block and the secondary ligand wherein the azido group and alkynyl group of the anchor ligand selection block and the secondary ligand are brought in close proximity by binding to the target protein;

(v) selecting the capture agent biligand that has an affinity with the target protein; and (vi) sequencing the secondary ligand; and optionally (c) identifying a tertiary ligand by the following steps:

(i) preparing a biligand selection block comprising an azido group or an alkynyl group; and (ii) repeating steps (b)(ii) to (b)(vi) using a third plurality, fourth plurality, etc., of candidate peptides until a capture agent having desired binding affinity to the target protein is obtained; and optionally (d) identifying a quarternary ligand and, optionally, additional ligands by the following steps:

(i) preparing a triligand selection block comprising an azido group or an alkynyl group; and (ii) repeating steps (c)(ii) to (c)(vi) using a fourth plurality, fifth plurality, etc., of candidate peptides until a capture agent having desired binding affinity to the target protein is obtained.

Also provided is a multiplex capture agent comprising two or more capture agents that bind specifically to two or more anti-gp41 antibodies. In one embodiment, the multiplex capture agent comprises a designed anchor ligand, a designed secondary ligand, optionally, a designed tertiary ligand and optionally, a designed quarternary ligand.

The disclosure also provides a method of diagnosing a disease comprising a) administering to the subject the multiplex capture agent of described above linked to a detectable moiety; and b) detecting the moiety linked to the multiplex capture agent in the subject; wherein detection of the moiety diagnoses a disease in the subject.

In either of these methods, the disease can be a viral infection. In certain embodiments, the viral infection is HIV.

Also provided is a method of diagnosing HIV infection, comprising:

a) administering to the subject a multiplex capture agent of described herein, wherein the multiplex capture agent is linked to a detectable moiety; and b) detecting the moiety linked to the multiplex capture agent in the subject; wherein detection of the moiety diagnoses the HIV infection in the subject.

(i). (C) Sensorgram and 1st order Hill fit to affinity data for A21-hnpfk (SEQ ID NO: 3) (ii).

Figure 5:
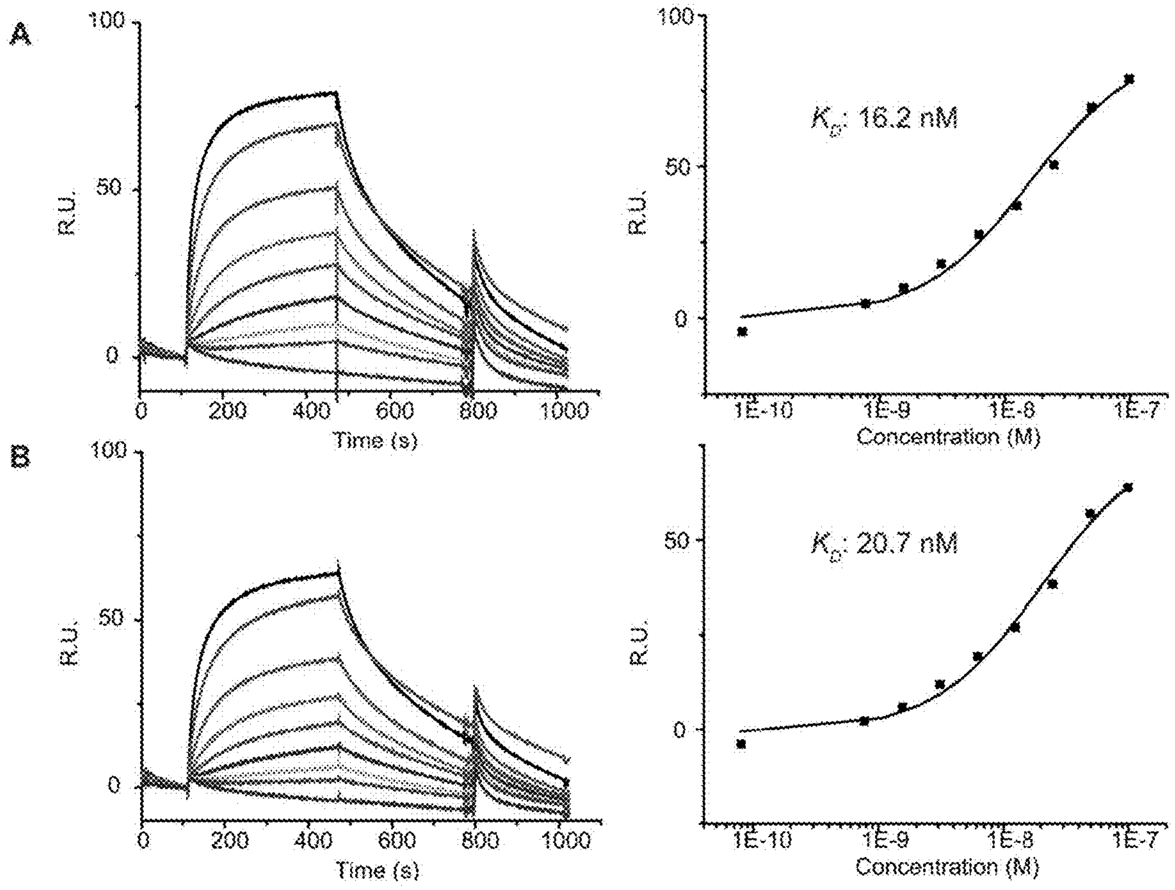

FIG. 5: Apparent affinity of A22 and biligand directed against 4B3 as determined by SPR. (A) Sensorgram and 1st order Hill fit to affinity data for A22. (B) Sensorgram and 1st order Hill fit to affinity data for A22-eihny (SEQ ID NO: 4) (iii).

Figure 6:
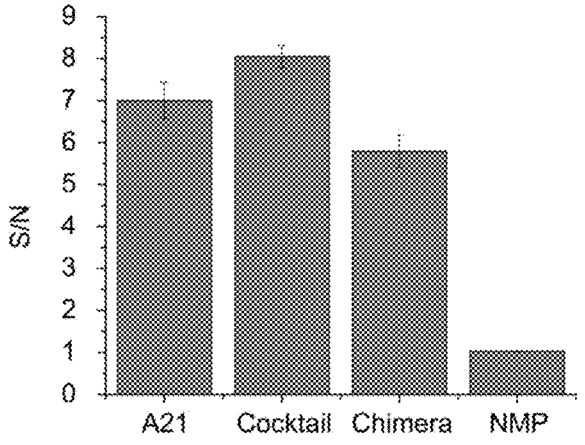
Figure 7:
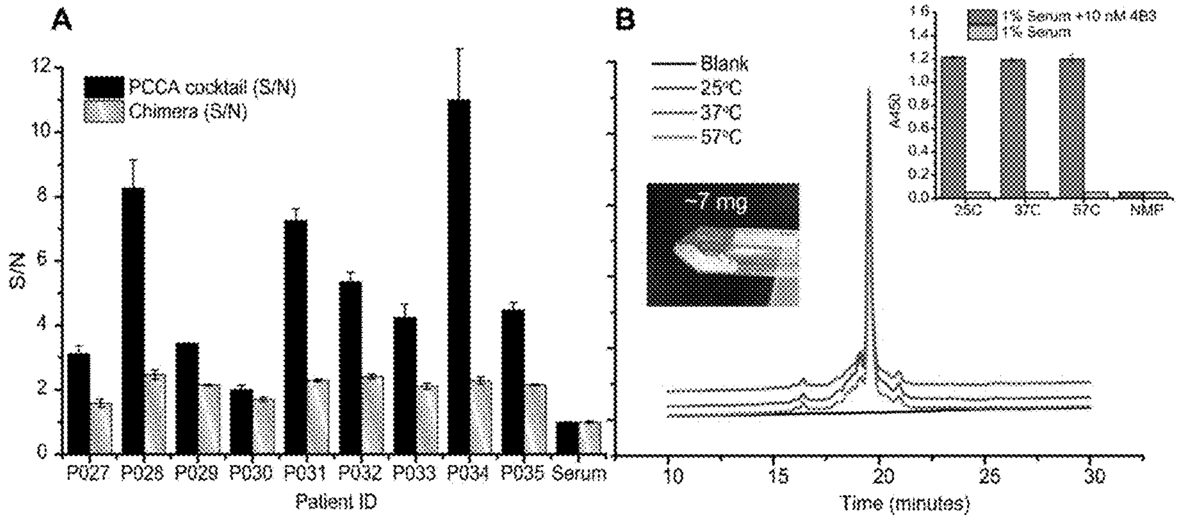

FIG. 6: Performance of PCC agent cocktail to detect 3D6 and 4B3 from human serum FIG. 7: (A) Performance of the PCC Agent cocktail, and (B) thermal stability and scale up of a cocktail component.

DETAILED DESCRIPTION

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

DEFINITIONS

"Amino" refers to the —$NH_2$ radical.

"Cyano" refers to the —CN radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Aminocarbonyl" refers to a radical of the formula —C(=O)$NR_aR_a$, where each $R_a$ is independently H, alkyl or a linker moiety.

"α-amino carbonyl" refers to a radical of the formula —C(=O)$CR_b$($NR_aR_a$)—, where each $R_a$ is independently H, alkyl or a linker moiety and $R_b$ is H or alkyl. In some embodiments, an alpha amino carbonyl is part of a cyclic moiety (e.g., peptide) where the carbonyl is within the ring and the amino ($NR^aR^a$) is exocyclic. For example, in certain embodiments an alpha aminocarbonyl is useful for Edman degradation of cyclic peptides.

α-amido carbonyl" refers to a radical of the formula —C(=O)$CR_b$(N(C=O)$R_aR_a$)—, where each $R_a$ is independently H, alkyl or a linker moiety and $R_b$ is H or alkyl. In some embodiments, an alpha amido carbonyl is part of a cyclic moiety (e.g., peptide) where the carbonyl is within the ring and the amido (N(C=O)$R^aR^a$) is exocyclic.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl.

Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (e.g., alkyl, alkylene, alkoxy, alkylamino, aminocarbonyl, α-aminocarbonyl, α-amidocarbonyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC$ (=O)$R_h$, —$NR_gC$(=O)$NR_gR_h$, —$NR_gC$(=O)$OR_h$, —$NR_gSO_2R_h$, —OC(=O) $NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with C(=O)$R_g$, C(=O)$OR_g$, C(=O)$NR_gR_h$, $CH_2SO_2R_g$, $CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable peptides of structure (I) or (I') being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled peptides of the invention, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled peptides can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed peptides. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts.

Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The compounds (peptides) of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. (D)-amino acids (also referred to as D-amino acids) are referred to herein in lower case letters (e.g. D-valine is referred to as "v"), while (L)-amino acids (also referred to herein as L-amino acids) are referred to in upper case letters (e.g. L-valine or valine is referred to as "V"). Glycine is non-chiral and is referred to as "G".

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

The term "capture agent" as used herein refers to a composition that comprises one or more target-binding moieties and which specifically binds to a target protein via those target-binding moieties. Each target-binding moiety exhibits binding affinity for the target protein, either individually or in combination with other target-binding moieties. In certain embodiments, each target-binding moiety binds to the target protein via one or more non-covalent interactions, including for example hydrogen bonds, hydrophobic interactions, and van der Waals interactions. A capture agent may comprise one or more organic molecules, including for example polypeptides, peptides, polynucleotides, and other non-polymeric molecules. In some aspects a capture agent is a protein catalyzed capture agent (PCC).

The term "epitope" as used herein refers to a distinct molecular surface of a protein (e.g., the HIV-1 gp41 protein). Typically, the epitope is a polypeptide and it can act on its own as a finite sequence of 10-40 amino acids. In the present disclosure, the epitope is targeted by endogenous anti-gp41 antibodies. The anti-gp41 antibodies are diagnostic indicators of HIV infection and therefore are targeted by the capture agents of the invention. As described herein, the anchor ligand of the capture agents of the invention are chemically modified variants of an immunogenic epitope of the HIV-1 gp41 protein.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, O-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The term "non-natural amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods.

The terms "specific binding," "selective binding," "selectively binds," or "specifically binds" as used herein refer to capture agent binding to an epitope on a predetermined antigen. Typically, the capture agent binds with an affinity ($K_D$) of approximately less than $10^{-7}$ M, such as approximately less than $10^{-8}$ M, $10^{-9}$ M or $10^{-10}$ M or even lower.

The term "$K_D$" as used herein refers to the dissociation equilibrium constant of a particular capture agent-antigen interaction. Typically, the capture agents of the invention bind to anti-gp41 antibodies with a dissociation equilibrium constant ($K_D$) of less than approximately $10^{-6}$ M, $10^{-7}$ M, such as less than approximately $10^{-8}$ M, $10^{-9}$ M or $10^{-10}$ M or even lower, for example, as determined using surface plasmon resonance (SPR) technology in a Biacore instrument using the antigen as the ligand and the antibody as the analyte, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The term "$k_d$" ($sec^{-1}$) as used herein refers to the dissociation rate constant of a particular antibody-antigen interaction. Said value is also referred to as the $k_{off}$ value.

The term "$k_a$" ($M^{-1} \times sec^{-1}$) as used herein refers to the association rate constant of a particular antibody-antigen interaction.

The term "$K_D$" (M) as used herein refers to the dissociation equilibrium constant of a particular antibody-antigen interaction.

The term "$K_A$" ($M^{-1}$) as used herein refers to the association equilibrium constant of a particular antibody-antigen interaction and is obtained by dividing the $k_a$ by the $k_d$.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status may serve as a predictor of the disease or event. For example, a change in health status may be an alteration in the expression level of a particular gene associated with a disease or event. Alternatively, a change in health status may not be associated with a particular disease or event.

The terms "treat," "treating," or "treatment" as used herein generally refer to preventing a condition or event, slowing the onset or rate of development of a condition or delaying the occurrence of an event, reducing the risk of developing a condition or experiencing an event, preventing or delaying the development of symptoms associated with a condition or event, reducing or ending symptoms associated with a condition or event, generating a complete or partial regression of a condition, lessening the severity of a condition or event, or some combination thereof.

An "effective amount" or "therapeutically effective amount" as used herein refers to an amount effective, at dosages and for periods of time necessary, to achieve a desired therapeutic result. A therapeutically effective amount of an antibody may vary according to factors such as the disease state, age, sex, and weight of the individual, and the ability of the capture agent to elicit a desired response in the individual.

The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab, Fv, Fab', $F(ab')_2$ and the like. A monoclonal antibody is an antibody that specifically binds to and is thereby defined as complementary to a single particular spatial and polar organization of another biomolecule which is termed an "epitope." In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

The term "stable" as used herein with regard to a capture agent protein catalyzed capture agent or pharmaceutical formulation thereof refers to the agent or formulation retaining structural and functional integrity for a sufficient period of time to be utilized in the methods described herein.

The term "synthetic" as used herein with regard to a protein catalyzed capture agent or capture agent refers to the capture agent has been generated by chemical rather than biological means.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

The term "gp41" as used herein refers to gp41 subunit of the envelope protein complex from HIV, which mediates membrane fusion during viral entry Development of Anti-gp41 Antibody Capture Agents Antibodies are currently the default detection agent for use in diagnostic platforms. However, antibodies possess several disadvantages, including high cost, poor stability, and, in many cases, lack of proper characterization and high specificity. The ideal replacement for use in diagnostic assays should be synthetic, stable to a range of thermal and chemical conditions, and display high affinity and specificity for the target of interest.

A high quality monoclonal antibody possesses low-nanomolar affinity and high target specificity. Interestingly, structural and genetic analyses of the antigen recognition surface have shown that the majority of the molecular diversity of the variable loops is contained in a single highly variable loop (CDR-H3). In humans, this loop ranges in size from 1-35 residues (15 on average), can adopt a wide range of structural conformations, and is responsible for most of the interactions with the antigen. The other five loops are significantly less diverse and adopt only a handful of conformations. This suggests that a carefully selected "anchor" peptide can dominate the mode and strength of the interaction between a capture agent and its target protein. It also suggests that other peptide components, while providing only modest contributions to the total interaction energy, can supply important scaffolding features and specificity elements.

In situ click chemistry is a technique in which a small molecule enzymatic inhibitor is separated into two moieties, each of which is then expanded into a small library—one containing acetylene functionalities, and the other containing azide groups. The enzyme itself then assembles the 'best fit' inhibitor from these library components by selectively promoting 1,3-dipolar cycloaddition between the acetylene and azide groups to form a triazole linkage (the 'click' reaction). The protein effectively plays the role of an extremely selective variant of the Cu(I) catalyst that is commonly used for such couplings. The enzyme promotes the click reaction only between those library components that bind to the protein in the right orientation. The resultant inhibitor can exhibit far superior affinity characteristics relative to the initial inhibitor that formed the basis of the two libraries.

Sequential in situ click chemistry extends the in situ click chemistry concept to enable the discovery of multiligand capture agents (see: USSN 20100009896, incorporated herein by reference). This process was used previously to produce a triligand capture agent against the model protein carbonic anhydrase II (CAII). Sequential in situ click chemistry has several advantages. First, structural information about the protein target is replaced by the ability to sample a very large chemical space to identify the ligand components of the capture agent. For example, an initial ligand may be identified by screening the protein against a large (>$10^6$ element) one-bead-one-compound (OBOC) peptide library, where the peptides themselves may be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final capture agent can then be scaled up using relatively simple and largely automated chemistries, and it can be developed with a label, such as a biotin group, as an intrinsic part of its structure. This approach permits the exploration of branched, cyclic, and linear capture agent architectures. While many strategies for protein-directed multiligand assembly have been described, most require detailed structural information on the target to guide the screening strategy, and most (such as the original in situ click approach), are optimized for low-diversity small molecule libraries.

As described herein, an iterative in situ click chemistry approach was utilized to synthesize a biligand capture agent that specifically binds anti-gp41 antibodies. This in situ click chemistry approach comprised two steps. First, a synthetic polypeptide derived from gp41 was selected as the initial screening target. Second, the secondary ligand selection process took advantage of the fact that an in situ click screen, in which an anchor ligand and full-length protein target are screened against a large OBOC library, will selectively generate multiligand products on the hit beads. This concept was expanded in the form of "product screens," in which the presence of on-bead clicked product is taken to be the signature of a hit bead. Such a product screen can be utilized to increase both the affinity and/or selectivity of the final multiligand capture agent.

The capture agents generated by the methods disclosed herein were found to display binding affinity for anti-gp41 antibodies. The capture agents were shown to function as both capture and detection agents in ELISA assays and efficiently immunoprecipitate anti-gp41 antibodies from dilute human serum.

Anti-gp41 Antibody Capture Agents

In certain embodiments, provided herein are biligand anti-gp41 antibody capture agents comprising two target-binding moieties. The first target-binding moiety is referred to as an anchor ligand, and the second is referred to as a secondary ligand. Also provided are triligand and tetraligand capture agents, wherein the third target-binding moiety is referred to as a tertiary ligand, and the fourth target-binding moiety is referred to as a quarternary ligand.

In certain embodiments, a target-binding moiety comprises one or more polypeptides or peptides. In certain of these embodiments, a target-binding moiety comprises one or more peptides comprising D-amino acids, L-amino acids, and/or amino acids substituted with functional groups selected from the group consisting of substituted and unsubstituted alkyl, substituted and unsubstituted azido, substituted and unsubstituted alkynyl, substituted and unsubstituted biotinyl, substituted and unsubstituted azioalkyl, substituted and unsubstituted polyethyleneglycolyl, and substituted and unsubstituted 1,2,3-triazole.

In certain embodiments, the anchor ligand and secondary ligand are linked to one another via a covalent linkage to form a capture agent biligand. In certain of these embodiments, the anchor ligand and secondary ligand are linked to one another via an amide bond or a 1,4-disubstituted-1,2,3-triazole linkage as shown below:

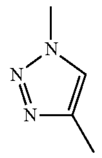

1,4-disubstituted-1,2,3-triazole linkage.

In those embodiments where the anchor and secondary ligands are linked to one another via a 1,4-disubstituted-1,2,3-triazole linkage, the 1,4-disubstituted-1,2,3-triazole linkage may be formed by Cu-Catalyzed Azide/Alkyne Cycloaddition (CuAAC).

In certain embodiments, the anchor and secondary ligands are linked to one another by a Tz4 linkage having the following structure:

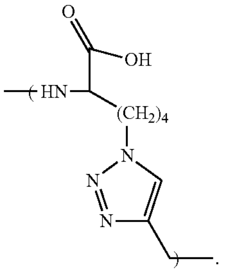

In certain embodiments, the anchor and secondary ligands are linked to one another by a Tz5 linkage having the following structure:

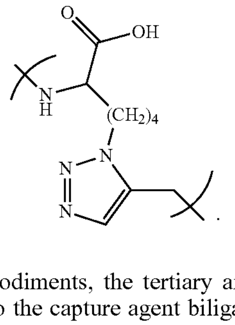

In certain embodiments, the tertiary and/or quarternary ligand is linked to the capture agent biligand by a covalent linkage, preferably via the secondary ligand in the biligand. In certain of these embodiments, the tertiary ligand and the biligand and/or the quarternary ligand and the tertiary ligand are linked to one another by a Tz4 linkage.

In those embodiments wherein one or more of the anchor, secondary, tertiary, and/or quarternary ligands are linked to one another via amide bonds, the amide bond may be formed by coupling a carboxylic acid group and an amine group in the presence of a coupling agent (e.g., O-(7-azabenzotriazol-1-yl)-N,N,N',N'-tetramethyluronium hexafluorophosphate (HATU), N-hydroxy-7-aza-benzotriazole (HOAt), or diisopropylethylamine (DIEA) in DMF).

In certain embodiments, the capture agents provided herein are stable across a range of reaction conditions and/or storage times. A capture agent that is "stable" as used herein maintains the ability to specifically bind to a target protein. In certain embodiments, the capture agents provided herein are more stable than an antibody binding to the same target protein under one or more reaction and/or storage conditions. For example, in certain embodiments the capture agents provided herein are more resistant to proteolytic degradation than an antibody binding to the same target protein.

In certain embodiments, the capture agents provided herein have a shelf-life of greater than six months, meaning that they are stable in storage for greater than six months. In certain of these embodiments, the capture agents have a shelf-life of one year or greater, two years or greater, or more than three years. In certain of these embodiments, the capture agents are stored as a lyophilized powder. In certain embodiments, the capture agents provided herein have a longer shelf-life than an antibody binding to the same target protein.

In certain embodiments, the capture agents provided herein are stable at temperatures ranging from about −80° to about 120° C. In certain of these embodiments, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C. In certain embodiments, the capture agents provided herein are stable across a wider range of temperatures than an antibody binding to the same target protein, and/or remain stable at a specific temperature for a longer time period than an antibody binding to the same target protein.

In certain embodiments, the capture agents provided herein are stable at a pH range from about 3.0 to about 8.0. In certain embodiments, the range is about 4.0 to about 7.0. In certain embodiments, the range is about 7.0 to about 8.0.

In certain embodiments, the capture agents provided herein are stable in human serum for more than 12 hours. In certain of these embodiments, the capture agents are stable in human serum for more than 18 hours, more than 24 hours, more than 36 hours, or more than 48 hours. In certain embodiments, the capture agents provided herein are stable for a longer period of time in human serum than an antibody binding to the same target protein. In certain embodiments, the capture agents are stable as a powder for two months at a temperature of about 60° C.

In certain embodiments, the capture agents provided herein may comprise one or more detection labels, including for example biotin, copper-1,4,7,10-tetraazacyclododecane-1,4,7,10-tetraacetic acid (copper-DOTA), $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C, $^{76}$Br, $^{123}$I, $^{131}$I, $^{67}$Ga, $^{111}$In and $^{99m}$Tc, or other radiolabeled products that may include gamma emitters, proton emitters, positron emitters, tritium, or covered tags detectable by other methods (i.e., gadolinium) among others. In a particular embodiment, the detection label is $^{18}$F. In certain embodiments, the capture agents may be modified to be used as imaging agents. The imaging agents may be used as diagnostic agents.

In certain embodiments, the capture agents provided herein may be modified to obtain a desired chemical or biological activity. Examples of desired chemical or biological activities include, without limitation, improved solubility, stability, bioavailability, detectability, or reactivity. Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In certain embodiments, the capture agent may be modified by modifying the synthesis blocks of the target-binding moieties before the coupling reaction.

Methods of Making/Screening Capture Agents

Provided herein in certain embodiments are methods of screening target-binding moieties and/or making capture agents that comprise these target-binding moieties. Methods for screening target-binding moieties and/or making capture agents that comprise these target-binding moieties can also be found in International Publication Nos. WO 2012/106671, WO 2013/033561, WO 2013/009869 and WO 2014/074907, each of which is incorporated by reference, herein, in their entireties.

The capture agent production methods disclosed herein begin with identification of a short-chain anchor peptide, then proceed by adding additional covalently coupled peptide ligands via a process that is promoted by the target protein. The specificity and inhibitory potency of the final multiligand capture agent are augmented by the peripheral peptide ligands.

In certain embodiments, the methods provided herein comprise the following steps:

(a) identifying an anchor ligand by the following steps:
  - (i) preparing a synthetic target polypeptide corresponding to an epitope of the target protein;
  - (ii) preparing a first plurality of candidate peptides to screen against the target polypeptide;
  - (iii) contacting the target polypeptide with the first plurality of candidate peptides;
  - (iv) selecting a candidate peptide with affinity for the target polypeptide as the anchor ligand, wherein the candidate peptide binds to the target polypeptide; and
  - (v) sequencing the anchor ligand;

(b) identifying a secondary ligand by the following steps:
  - (i) preparing an anchor ligand selection block comprising the anchor ligand and an azido group or an alkynyl group;
  - (ii) preparing a second plurality of candidate peptides to select a secondary ligand for the target protein, the second plurality of peptides comprising an azido group or an alkynyl group if the anchor ligand selection block comprises an alkynyl group and azido group respectively;
  - (iii) contacting the anchor ligand selection block and the second plurality of peptides with the target protein;
  - (iv) providing a capture agent biligand by forming a disubstituted 1,2,3-triazole linkage between the anchor ligand selection block and the secondary ligand wherein the azido and alkynyl group of the anchor ligand selection block and the secondary ligand are brought in close proximity by binding to the target protein;
  - (v) selecting the capture agent biligand that has an affinity with the target protein; and
  - (vi) sequencing the secondary ligand;

(c) identifying a tertiary ligand by the following steps:
(i) preparing a biligand selection block comprising an azido group or an alkynyl group; and
(ii) repeating steps (b)(ii) to (b)(vi) using a third plurality of candidate peptides until a capture agent having desired binding affinity to the target protein is obtained;
(d) identifying a quarternary ligand and, optionally, additional ligands by the following steps:
(i) preparing a triligand selection block comprising an azido group or an alkynyl group; and
(ii) repeating steps (c)(ii) to (c)(vi) using a fourth plurality, fifth plurality, etc., of candidate peptides until a capture agent having desired binding affinity to the target protein is obtained.

In certain embodiments, one or more of the above steps may be omitted. For example, in certain embodiments a known anchor ligand is used. In these embodiments, step (a) is omitted, and the known anchor ligand is used to identify the secondary ligand in step (b). In those embodiments where the target protein is anti-gp41 antibodies, the anchor ligand may comprise the peptide sequenceIWCGS-GKLICTTA (SEQ ID NO: 1). In certain embodiments, this anchor ligand may be modified with an N- or C-terminal biotin prior to step (b).

In certain embodiments, steps (b)(ii) to (b)(vi) are repeated one time, resulting in production of a capture agent triligand.

In certain embodiments, the first, second, and any additional pluralities of candidate peptides comprise a "one bead one compound" (OBOC) peptide library, wherein the peptides comprise 5 to 7 D-amino acid residues and coupled with a D-propargylglycine at the N-terminus. In certain embodiments, the pluralities of candidate peptides may be different. In other embodiments, one or more of the pluralities may contain the same peptide pool.

In certain embodiments, the methods provided herein utilize a known anchor ligand. In a particular embodiment, the anchor ligand comprises the sequence IWCGS-GKLICTTA (SEQ ID NO: 1).

In certain embodiments, the anchor ligand used for the screening process may be modified with a biotin. For example, the anchor ligand used for the screening process may be Biotin-$PEG_5$-IWCGSGKLICTTA(SEQ ID NO: 1)-Pra.

In one embodiment, the screening/preparation process comprises the following steps:
a) contacting the anti-gp41 antibody with the Biotin-$(PEG)_5$- IWCGSGKLICTTA(SEQ ID NO: 1)-Pra anchor ligand to provide an antibody-anchor complex;
b) contacting the antibody-anchor complex with a first plurality of candidate peptides to select a secondary ligand, the peptides coupled with an Az4-$CONH_2$ moiety at its N-terminus;
c) providing a capture agent biligand by forming a disubstituted-1,2,3-triazole linkage between the anchor ligand selection block and the secondary ligand, wherein the azido and alkynyl group of the anchor ligand selection block and the secondary ligand are brought in close proximity by binding to the target protein to provide a bead modified with the capture agent biligand;
d) selecting the beads modified with the capture agent biligand;
e) removing the capture agent biligands from the beads;
f) sequencing the secondary ligand of the capture agent biligand;
g) preparing the capture agent biligand with an N-terminal Biotin-$(PEG)_5$ label and a C-terminal Az4; and
h) repeating the above steps until an anti-gp41 antibody capture agent having the desired properties is identified.

In certain embodiments, methods are provided for synthesizing a capture agent as provided herein. In certain embodiments, these methods comprise:
a) preparing a synthesis block of a target-binding moiety, the synthesis block comprising the target-binding moiety and at least one reactive group that can form a desired linkage with another synthesis block, wherein:
i) the linkage is selected from the group consisting of amide linkage, 1,4-disubstituted 1,2,3-triazole linkage, and 1,5-disubstituted 1,2,3-triazole linkage; and
ii) all other active functional groups of the target-binding moiety are protected to avoid undesired reactions; and
b) coupling the synthesis blocks of the target-binding moieties to provide the capture agent.

Methods for Targeting Specific Antibodies

An approach for synthesizing molecules that bind to antibodies is described and demonstrated. The invention includes first preparing a peptide or polypeptide fragment corresponding to the epitope targeted by the antibody. That polypeptide can be site-specifically modified by either substituting one of the naturally occurring amino acids with an artificial amino acid, or the polypeptide fragment is modified after synthesis by chemically altering a specific amino acid. In both cases, the polypeptide can be modified to incorporate either an alkyne or an azide chemical group near the site-specific modification. That azide (or alkyne) containing fragment is then incubated with a very large molecular library. This library, while typically chemically diverse, is also characterized by the fact that each element contains an alkyne (or, instead, each element contains an azide) group. The incubation can be done under conditions that the modified polypeptide fragment can provide a catalytic scaffold for promoting the covalent coupling between select library elements and the polypeptide fragment. In this embodiment, it promotes this coupling by catalyzing the formation of a triazole linkage that is the reaction product of the acetylene and azide groups. According to several embodiments, the selectivity of this catalyzed process is very high. This means that only a very small fraction of the elements in the molecular library will be coupled. Those elements are identified through analytical techniques, and then tested for binding to the polypeptide fragment, or to the entire protein biomolecule from which the polypeptide fragment was extracted. This approach provides a route towards identifying molecules that selectively bind to the intended epitope of the protein target. Approaches known in the art may then be utilized to increase the selectivity and the affinity of the identified binders, without sacrificing their epitope selective binding characteristics.

The following steps are performed in one embodiment of the process. An antibody target (1) is selected for developing capture agent molecule that will bind to that antibody. The antibody is known to target a protein epitope with a known sequence of amino acids (2). A polypeptide fragment (3) corresponding to the epitope of the protein is synthesized, but with two modifications. First, (3) is either substituted or chemically modified so as to provide an azide or alkyne group. Second, a site on the polypeptide is modified (4) with a label (a fluorophore or biotin group, for example) for use during the screening steps. There are many ways through which this label can be introduced.

If a molecular library of 1 million molecules, designed to span a broad chemical space, is incubated with a ~50-100 nM concentration solution of the modified polypeptide fragment (3), under standard blocking conditions to prevent non-selective binding, then that screen will generate about 20-100 hit molecules. Of those hit molecules, a small number (1-10) will be molecules that specifically bind to the antibody of interest. Approaches described herein can then be utilized to increase the affinity and specificity of those antibody-specific binders.

In Vitro

For detection of anti-gp41 antibodies in solution, a capture agent of the invention can be detectably labeled, then contacted with the solution, and thereafter formation of a complex between the capture agent and the antibody target can be detected. As an example, a fluorescently labeled capture agent can be used for in vitro anti-gp41 antibody detection assays, wherein the capture agent is added to a solution to be tested for anti-gp41 antibodies under conditions allowing binding to occur. The complex between the fluorescently labeled capture agent and the anti-gp41 antibody target can be detected and quantified by, for example, measuring the increased fluorescence polarization arising from the complex-bound peptide relative to that of the free peptide.

Alternatively, a sandwich-type "ELISA" assay can be used, wherein a capture agent is immobilized on a solid support such as a plastic tube or well, then the solution suspected of containing anti-gp41 antibodies is contacted with the immobilized binding moiety, non-binding materials are washed away, and complexed polypeptide is detected using a suitable detection reagent recognizing the anti-gp41 antibodies.

For detection or purification of soluble anti-gp41 antibodies from a solution, capture agents of the invention can be immobilized on a solid substrate such as a chromatographic support or other matrix material, then the immobilized binder can be loaded or contacted with the solution under conditions suitable for formation of a capture agent/anti-gp41 antibody complex. The non-binding portion of the solution can be removed and the complex can be detected, for example, using an anti-IgG antibody, or an anti-binding polypeptide antibody, or the anti-gp41 antibodies can be released from the binding moiety at appropriate elution conditions.

In Vivo

Diagnostic Imaging

A particularly preferred use for the capture agents of the invention is for creating visually readable images of anti-gp41 antibodies in a biological fluid, such as, for example, in human serum. The anti-gp41 antibody capture agents disclosed herein can be converted to imaging reagents by conjugating the capture agents with a label appropriate for diagnostic detection. Preferably, a capture agent exhibiting much greater specificity for anti-gp41 antibodies than for other serum proteins is conjugated or linked to a label appropriate for the detection methodology to be employed. For example, the capture agent can be conjugated with or without a linker to a paramagnetic chelate suitable for Magnetic Resonance Imaging (MRI), with a radiolabel suitable for x-ray, Positron Emission Tomography (PET), Single Photon Emission Computed Tomography (SPECT) or scintigraphic imaging (including a chelator for a radioactive metal), with an ultrasound contrast agent (e.g., a stabilized microbubble, a microballoon, a microsphere or what has been referred to as a gas filled "liposome") suitable for ultrasound detection, or with an optical imaging dye.

In another embodiment, rather than directly labeling a capture agent with a detectable label or radiotherapeutic construct, one or more peptides or constructs of the invention can be conjugated with for example, avidin, biotin, or an antibody or antibody fragment that will bind the detectable label or radiotherapeutic.

Therapeutic Applications

Provided herein in certain embodiments are methods of using the anti-gp41 antibody capture agents disclosed herein to identify, detect, quantify, and/or separate anti-gp41 antibodies in a biological sample. In certain embodiments, these methods utilize an immunoassay, with the capture agent replacing an antibody or its equivalent. In certain embodiments, the immunoassay may be a Western blot, pull-down assay, dot blot, or ELISA.

A biological sample for use in the methods provided herein may be selected from the group consisting of organs, tissue, bodily fluids, and cells. Where the biological sample is a bodily fluid, the fluid may be selected from the group consisting of blood, serum, plasma, urine, sputum, saliva, stool, spinal fluid, cerebral spinal fluid, lymph fluid, skin secretions, respiratory secretions, intestinal secretions, genitourinary tract secretions, tears, and milk. The organs include, e.g., lymphoid organs. Tissues include, e.g., mucosal tissues.

Provided herein in certain embodiments are methods of using the anti-gp41 antibody capture agents disclosed herein to diagnose and/or classify (e.g., stage) a condition associated with anti-gp41 antibodies, including for example various HIV infections. In certain of these embodiments, the methods comprise (a) obtaining a biological sample from a subject; (b) measuring the presence or absence of anti-gp41 antibodies in the sample with the anti-gp41 antibody capture agent; (c) comparing the levels of anti-gp41 antibodies to a predetermined control range for anti-gp41 antibodies; and (d) diagnosing a condition associated with anti-gp41 antibodies based on the difference between anti-gp41 antibody levels in the biological sample and the predetermined control.

Therapeutic agents and the anti-gp41 antibody capture agents disclosed herein can be linked or fused in known ways, optionally using the same type of linkers discussed elsewhere in this application. Preferred linkers will be substituted or unsubstituted alkyl chains, amino acid chains, polyethylene glycol chains, and other simple polymeric linkers known in the art. More preferably, if the therapeutic agent is itself a protein, for which the encoding DNA sequence is known, the therapeutic protein and anti-gp41 antibody binding polypeptide can be coexpressed from the same synthetic gene, created using recombinant DNA techniques, as described above. The coding sequence for the anti-gp41 antibody binding polypeptide can be fused in frame with that of the therapeutic protein, such that the peptide is expressed at the amino- or carboxy-terminus of the therapeutic protein, or at a place between the termini, if it is determined that such placement would not destroy the required biological function of either the therapeutic protein or the anti-gp41 antibody binding polypeptide. A particular advantage of this general approach is that concatamerization of multiple, tandemly arranged anti-gp41 antibody capture agents is possible, thereby increasing the number and concentration of anti-gp41 antibody binding sites associated with each therapeutic protein. In this manner, anti-gp41 antibody binding avidity is increased, which would be expected to improve the efficacy of the recombinant therapeutic fusion protein.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1

Antibody-targeted PCC Development

For the present work, the two reacting species are peptides—one peptide (the anchor) is a chemically modified variant of a conserved, immunogenic epitope on the HIV-1 gp41 protein, and the second peptide is selected via an in situ click screen from a large ($10^6$ element) one-bead-one-compound (OBOC) peptide library. The protein targets are human monoclonal antibodies raised against variants of the gp41 epitope represented by the anchor peptide.

Figure 2:
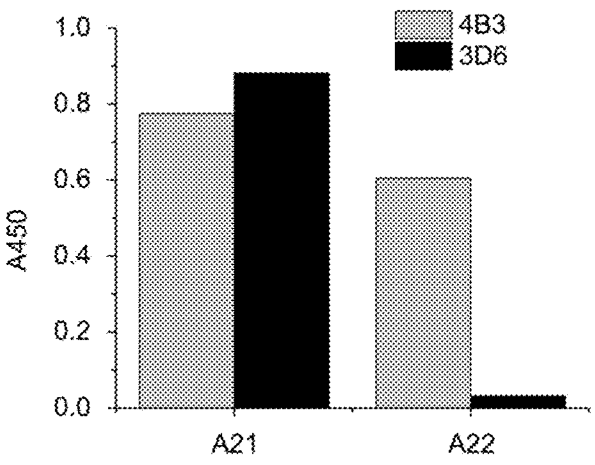
FIG. 2: Differential detection of 3D6 and 4B3 by anchor ligands.

The PCC Agents developed here were designed to capture antibodies that are selective for residues 600-612 (IWCGSGKLICTTA) (SEQ ID NO: 1) of gp41. Studies have shown that a large fraction of HIV-1-positive patients develop antibodies against this epitope. The strategy for sampling the polyclonal diversity of such antibodies was to develop PCC Agents that exhibited both differential, as well as similar avidities for human monoclonal antibodies (mAbs) raised against different parts of this epitope. A key decision in this regard involves the selection of the anchor peptides from which the PCC Agents are developed. For this task, the polypeptide fragment corresponding to residues 600-612 of gp41 was modified with artificial amino acids at multiple locations, and the ability of these modified peptides was tested to detect two different monoclonal anti-gp41antibodies 3D6 and 4B3 (Polymun, Klosterneuburg, Austria). The 3D6 mAb was raised against the epitope SGKLIC (SEQ ID NO: 6), whereas the 4B3mAb was raised against SGKLICTTA (SEQ ID NO: 7). One anchor peptide, A21, was synthesized by adding a propargyl glycine (Pra) residue at the C-terminus of the residues 600-612 of gp41. This anchor peptide was also N-terminally tagged with a polyethylene glycol (PEG) oligomer bridge and a biotin label. For a second anchor peptide (A22), Leu-607 was substituted with Pra. A22 also included an N-terminal PEG-biotin label. Relative affinities of A21 and A22 for 3D6 and 4B3 were determined by sandwich ELISA. Biotinylated anchor ligands A21 and A22 were immobilized on streptavidin-coated 96-well plated at a concentration of 100 nM, and incubated with the solutions of target anti-HIV antibodies 3D6 and 4B3 at 100 nM in TBS. Captured antibody was detected by peroxidase-conjugated anti-human IgG antibody. A22 differentially detected 3D6 ($K_{d\ >10}$ μM) and 4B3 ($K_d$=1-50 nM) (FIG. 2). A21 and A22 were then separately developed into PCC agents against 3D6 and 4B3, respectively.

Figure 3:
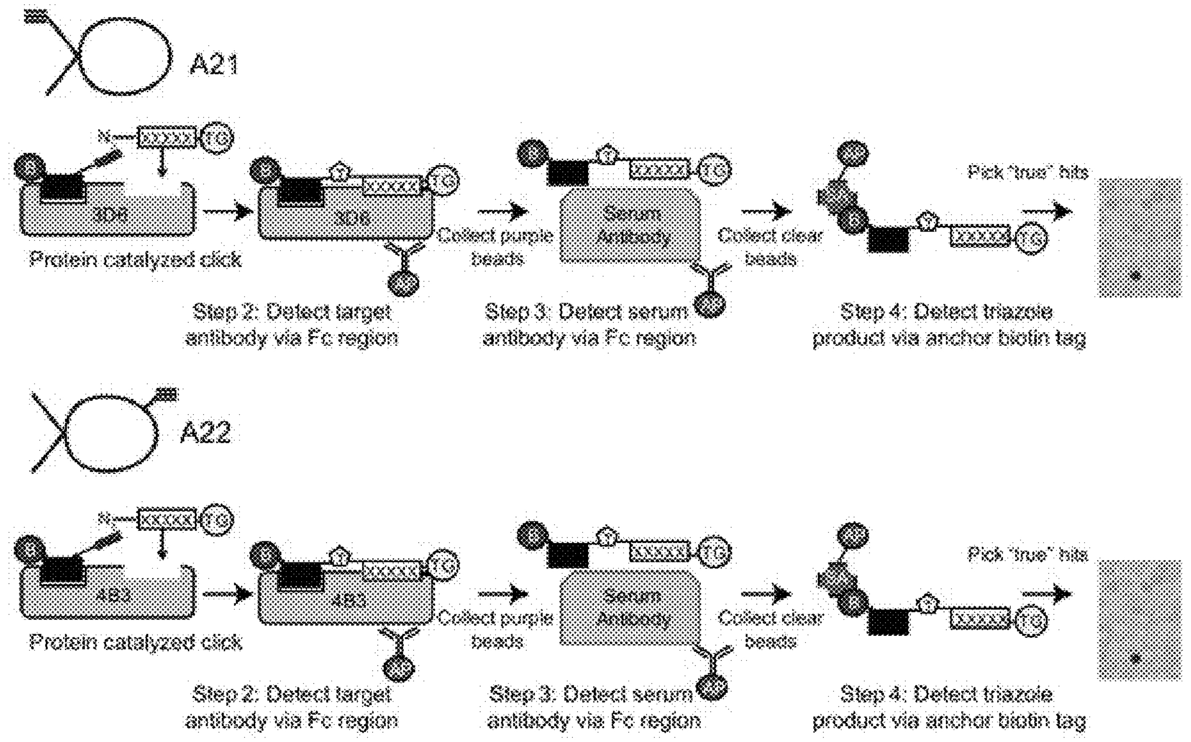
FIG. 3: Screening strategy for selecting capture agents against anti-HIV antibodies 3D6 and 4B3 using anchor ligands A21 and A22 respectively.

The in situ click screens are illustrated in FIG. 3. The target IgG is incubated with an excess of the selected anchor peptide and a large OBOC library at 4° C. overnight. The OBOC library is synthesized on TentaGel resin (Rapp Polymere, Tuebingen, Germany), and is a comprehensive library of 5-mers with a 6th amino acid at the N-terminus presenting an azide functionality. To help ensure chemical and biochemical stability, the OBOC library is comprised of non-natural (D) stereoisomers of the 20 natural amino acids, excluding cysteine and methionine. The in situ screen is designed to identify a secondary (2°) peptide that, when coupled to the anchor, forms a biligand with increased selectivity and/or affinity for the target IgG. The screen proceeds stepwise. In the first step (not shown in FIG. 3) the OBOC library is cleared of beads that exhibit non-specific binding to alkaline phosphatase-conjugated streptavidin (SA-AP), which is used as a detection reagent in a later step. Step 2 is a target screen, and so is designed to detect the presence of the bound IgG target to specific beads, and defines possible hits. The step 3 screen is designed to remove those beads from the pool of potential hits that also exhibit binding to off-target serum proteins. Step 4 is called a product screen, and is unique to sequential in situ click screens. This screen is designed to detect for the presence of in situ clicked reaction products, which are those hit beads containing the triazole-linked anchor peptide. Typically, Step 2 yields a few hundred hits (~0.05% of the OBOC library). Step 3 reduces that pool by a factor of 2 or 3 to about 100 hits, and Step 4 further reduces the number of hits to around 10. This is a manageable number, meaning that each hit can be separately synthesized as a biligand using Cu(I) catalyzed click chemistry to couple the anchor and 2° peptides.

Example 2

Evaluation of Antibody-targeting Peptides

Figure 4:
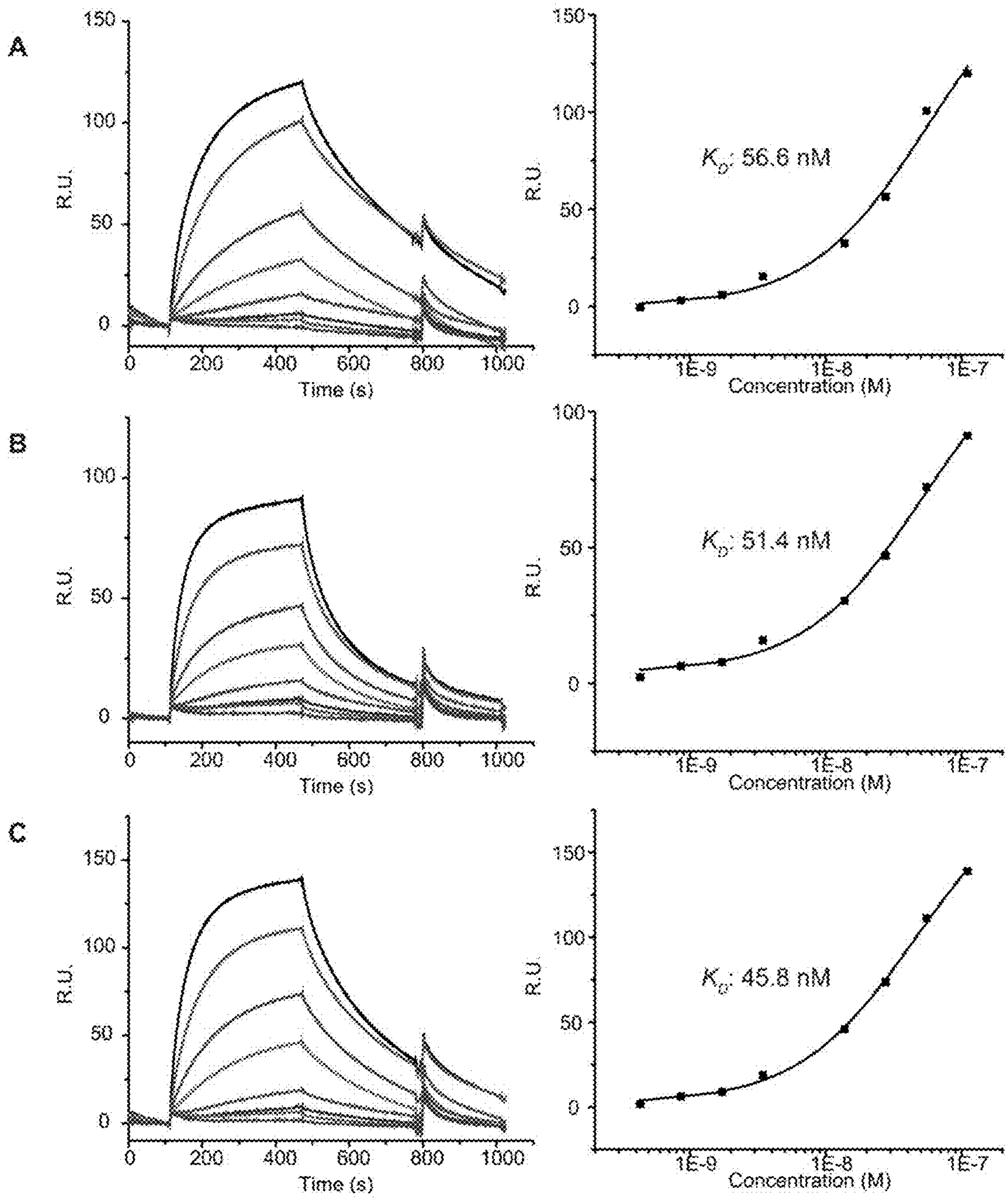
FIG. 4: Apparent affinity of A21 and biligands directed against 3D6 as determined by SPR. (A) Sensorgram and 1st order Hill fit to affinity data for A21. (B) Sensorgram and 1st order Hill fit to affinity data for A21-nidnG (SEQ ID NO: 2)

The performance of the biligands was characterized using immunoprecipitation (pulldown) assays detected by Western blotting from spiked serum samples for specificity, and sandwich ELISAs and surface plasmon resonance (SPR) assays for affinity estimations (FIGS. 4 and 5). A complete list of the hits for the A21/3D6 and A22/4B3 screens is given in Table 1.

The selected secondary ligands corresponding to (i), (ii), and (iii) are in bold.

TABLE 1

List of hits for the A21/3D6 and A22/4B3 screens

| | X1 | X2 | X3 | X4 | X5 | SEQ ID NO: |
|---|---|---|---|---|---|---|
| Az4 | d | k | G | l | p | 8 |
| Az4 | v | a | d | P | a | 9 |
| Az4 | n | i | d | n | G | 2 |
| Az4 | p | G | v | t | f | 10 |
| Az4 | s | r | r | r | s | 11 |
| Az4 | d | q/e | G | a | f | 12 |
| Az4 | y | w | d | y | n | 13 |
| Az4 | h | l | l | y | q | 14 |
| Az4 | s | G | a | q | s | 15 |
| Az4 | d | d | w | a | i | 16 |
| Az4 | q | i | d | l | r | 17 |
| Az4 | t | f | L | q | s | 18 |
| Az4 | h | n | p | f | k | 3 |
| Az4 | w | G | e | h | p | 19 |
| Az4 | q | n | d | w | K | 20 |
| Az4 | l | t | s | r | Y | 21 |
| Az4 | d | i | k | s | p | 22 |
| Az4 | e | i | h | n | y | 4 |
| Az4 | q | p | i | d | q | 23 |
| Az4 | k | i | d | r | v | 24 |
| Az4 | q | s | p/d | w | l | 25 |
| Az4 | e | q | t | f | d | 26 |

Figure 1:
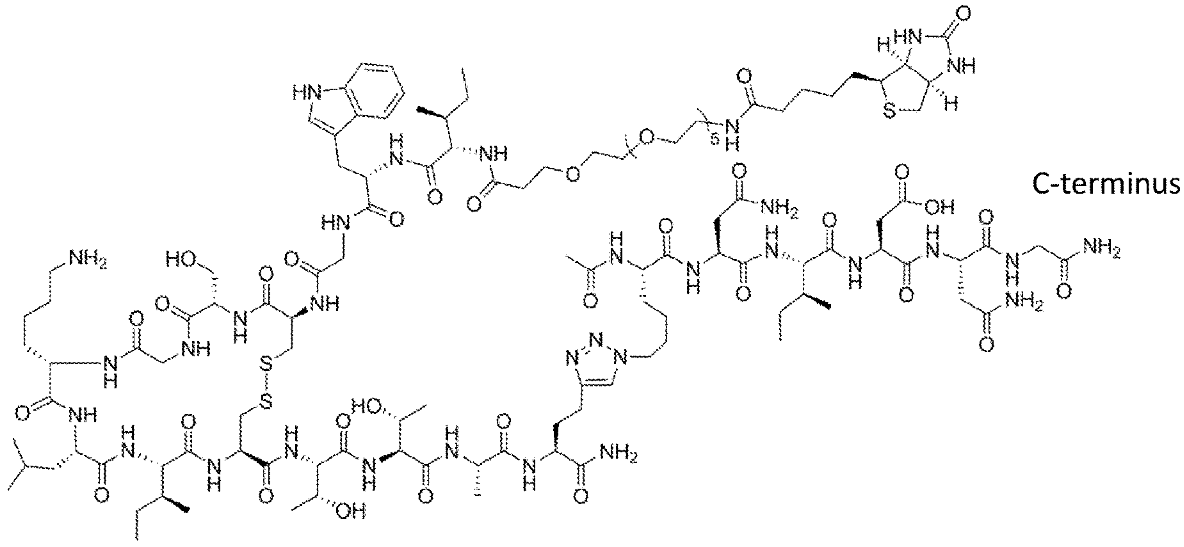
FIG. 1: The structures of peptide ligands in a PCC agent "cocktail" (i.e., a composition comprising two or more capture agents): (i) Biotin-$PEG_5$-IWCGSGKLICTTA(SEQ ID NO: 1) -Pra-($T_z$-$Az_4$-nidnG (SEQ ID NO: 2)-$CONH_2$)-$CONH_2$; (ii) Biotin-$PEG_5$-IWCGSGKLICTTA (SEQ ID NO: 1)-Pra-($T_z$-$Az_4$-hnpfk(SEQ ID NO: 3)-$CONH_2$)-$CONH_2$; (iii) Biotin-$PEG_5$-IWCGSGKLICTTA(SEQ ID NO: 1)-Pra-($T_z$-$Az_4$-eihny(SEQ ID NO: 4)-$CONH_2$)-ICTTA (SEQ ID NO: 5)-$CONH_2$.
Figure 1:
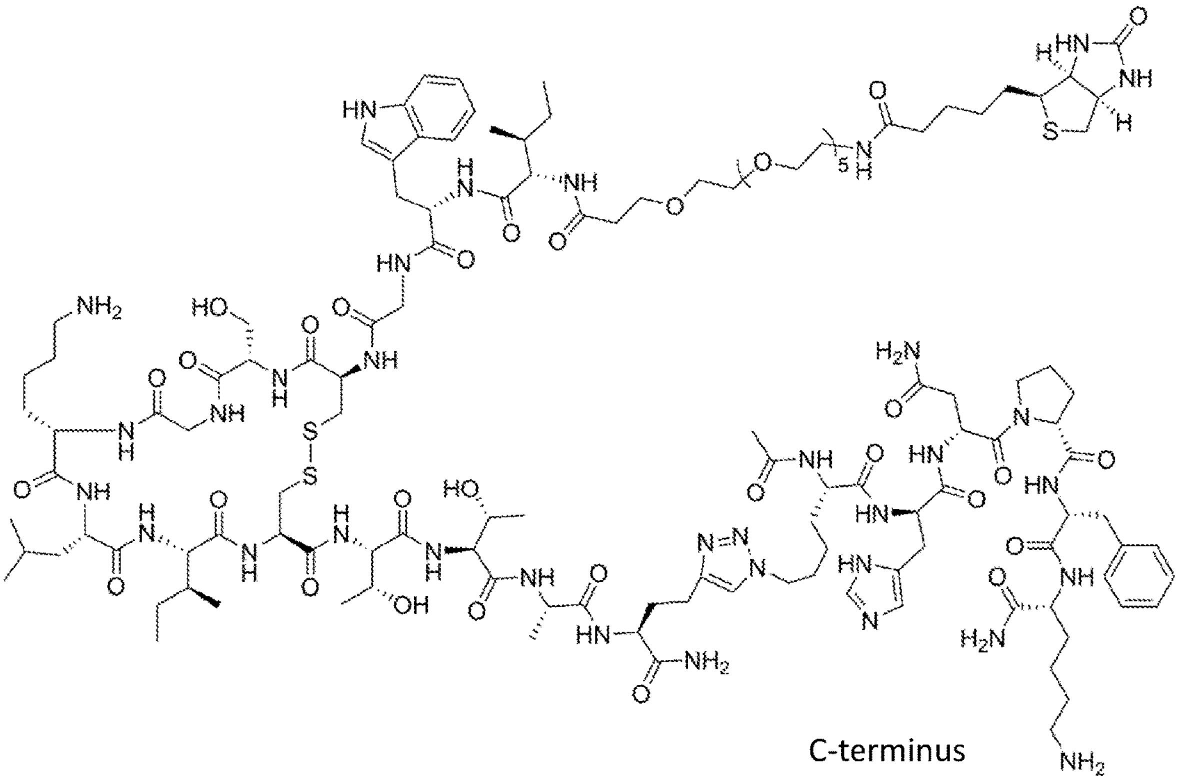
Figure 1:
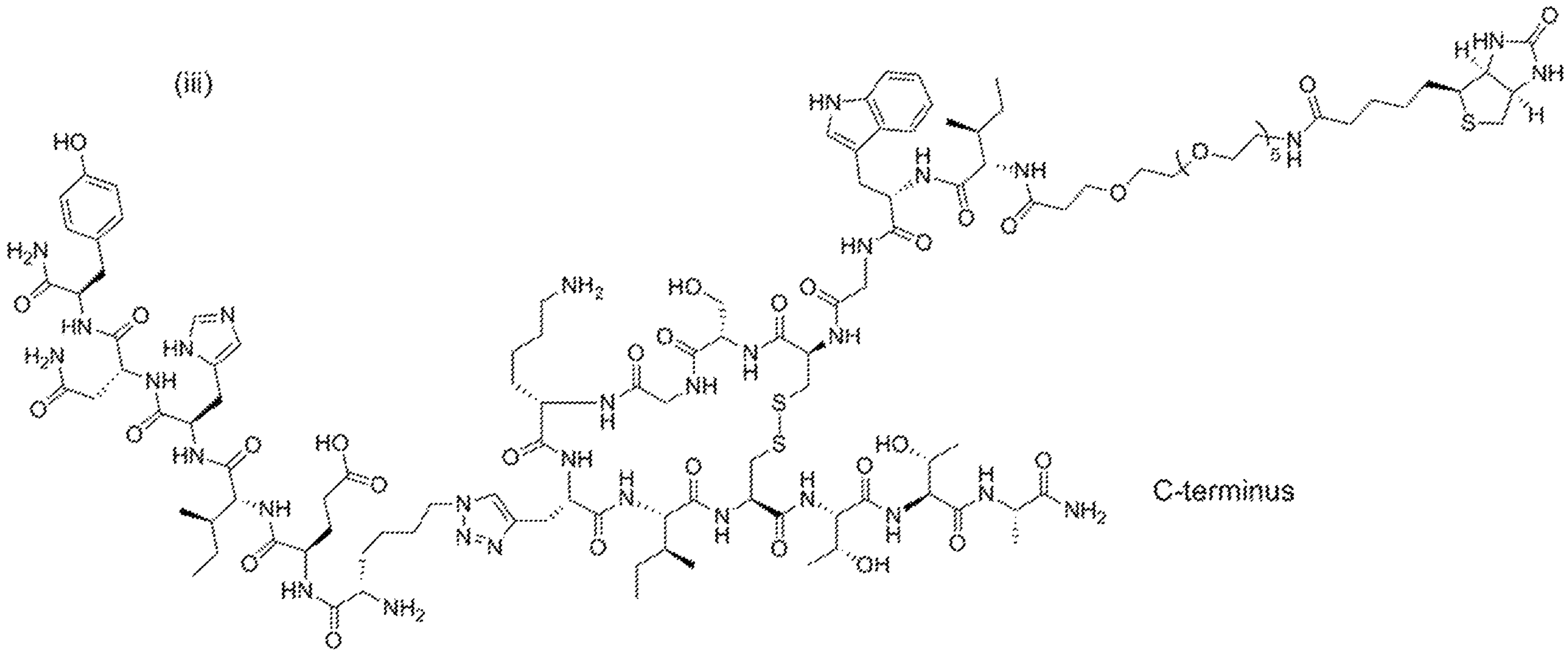

This approach yielded two equivalently performing biligands against 3D6, and one biligand against 4B3 (FIGS. 4 and 5). FIG. 4A shows a sensorgram and $1^{st}$ order Hill fit to affinity data for A21. FIG. 4B shows a sensorgram and $1^{st}$ order Hill fit to affinity data for A21-nidnG (SEQ ID NO: 2) (i). FIG. 4C shows a sensorgram and $1^{st}$ order Hill fit to affinity data for A21-hnpfk (SEQ ID NO: 3) (ii). FIG. 5A shows sensorgram and $1^{st}$ order Hill fit to affinity data for A22. FIG. 5B shows sensorgram and $1^{st}$ order Hill fit to affinity data for A22-eihny (SEQ ID NO: 4) (iii). These three PCC agents (FIG. 1) were combined, in equal parts, to form a capture agent cocktail. The cocktail slightly outperformed both the standard commercial chimeric antigen and A21, when tested against healthy human serum spiked with both 3D6 and 4B3 (FIG. 6). A21 is the equivalent of the original antigenic epitope of gp41.

The PCC Agent cocktail and the standard antigen were co-evaluated against a panel of clinical samples using sandwich ELISAs. Serum samples were collected from nine HIV-1-positive patients in Southern California. The standard antigen is a recombinant chimeric protein containing a fragment of HIV-1 gp41 (residues 546-692), the "O" group HIV-1 gp41 immunodominant region (residues 580-623), and a fragment of HIV-2 gp36 (residues 591-617). A good performance of this chimeric antigen has been reported (see, e.g., Chin C D, Laksanasopin T, Cheung Y K, Steinmiller D, Linder V, et al. (2011): Microfluidics-based diagnostics of infectious diseases in the developing world. Nat Med 17: 1015-1019). For the comparison assays, streptavidin-coated 96-well plates were saturated with the PCC Agent cocktail or chemically biotinylated chimera in triplicates. Serum samples were diluted to 1% v/v in Tris-buffered saline (TBS) supplemented with 0.1% w/v bovine serum albumin (BSA), and incubated in the wells for 1 hr at room temperature. Unbound proteins were washed off and captured IgG was detected with a peroxidase-conjugated mouse monoclonal anti-human IgG-Fc antibody. The comparison assay results for the patient serum samples along with a healthy control are shown in FIG. 7A. Comparative performance of the PCC Agent cocktail versus the commercial chimeric protein, was determined using sandwich ELISAs to detect anti-HIV-1 IgGs from a panel of sera samples collected from nine HIV-positive patients. The absorbance at 450 nm (A450) for each sample is normalized against the A450 for the healthy control, to yield a measurement of the signal-to-noise ratio of the assay. The PCC Agent cocktail, which is designed to capture a subset of anti-gp41 IgGs, exhibits superior performance for every sample, even though the chimeric protein is designed to capture antibodies against multiple HIV-1-associated epitopes (those containing fragments of HIV-1 gp41, "O" group HIV-1 gp41 immunodominant region, and HIV-2 gp39). For the assays, the PCC agent cocktail and the biotinylated chimeric antigen were immobilized on a streptavidin-coated 96-well plate and incubated with diluted patient serum (1% v/v). Captured anti-HIV antibodies were detected using peroxidase-conjugated anti-human IgG antibody. The signal-to-noise (S/N) ratio in these assays is defined as the measured ELISA signal for a given patient sample, divided by that for the healthy control. The PCC Agent cocktail performed at least as well, and typically much better, than the standard chimeric protein antigen. The average S/N improvement by the cocktail PCC agent over the chimeric antigen was a factor of 2.5.

We then tested the PCC Agents for thermal stability. The PCC Agent cocktail component (iii) were synthesized at a large scale for an academic setting (~7 mg, FIG. 7B) and the lyophilized samples were stored under $N_2$ at 25° C., 37° C., or 57° C. for 58 days. The samples were then analyzed by HPLC to determine the presence of any degradation product. The traces of the peptide at each temperature are nearly identical, indicating little to no degeneration at these temperatures (FIG. 7B). The performance of these stored PCC Agents was then also tested in an ELISA, with no detectable loss of performance (FIG. 7B).

Example 3

Anchor Synthesis

A21 and A22: The anchor peptides were synthesized C→N on 200-300 mgs of Rink amide resin (AnaSpec, Fremont, Calif.) with a Titan peptide synthesizer using standard Fmoc chemistry. The synthesis used Fmoc and side chain protected L amino acids (Aaptec, Louisville, Ky.), Fmoc protected propargylglycine (Pra) (Aaptec, Louisville, Ky.), $PEG_5$ (EMD Millipore, Germany), and biotin (Sigma-Aldrich, St. Louis, Mo.). The finished peptides were side-chain deprotected and cleaved from resin in a mixture of 95% v/v trifluoroacetic acid (TFA) (Sigma-Aldrich, St. Louis, Mo.), 5% v/v $dH_2O$, and 5% triethylsilane (TES) (Sigma-Aldrich, St. Louis, Mo.), and precipitated in diethyl ether. $Cu(Phen)_3$ stock solution was prepared by mixing 150 mM Cu(II) sulfate pentahydrate (Sigma-Aldrich, St. Louis, Mo.) and 500 mM 1,10-phenanthroline (Sigma-Aldrich, St. Louis, Mo.) in 4:1 $H_2O$:Ethanol. The ether-precipitated ligands were cyclized by stirring the cleaved peptides dissolved in ~5 mL acetonitrile (ACN) overnight with 1 mL of the $Cu(Phen)_3$ stock solution. The cyclization mixtures were lyophilized, and the final peptide products were purified using reverse phase (RP) HPLC. MALDI-TOF MS: A21: Expected mass $[M+H]^+$=2006.96, Observed mass $[M+H]^+$=2006.24. A22: Expected mass $[M+H]^+$=1892.89, Observed mass $[M+H]^+$=1892.85

OBOC Screens: All screens used naïve one-bead-one-compound (OBOC) D-pentapeptide libraries on TentaGel resin (TG) (Rapp Polymere, Tuebingen, Germany) of the form $NH_2$-$Az_4$-$X_1X_2X_3X_4X_5$-TG, excluding cysteine and methionine, where $Az_4$ is L-azidolycine. Libraries were synthesized on a Titan peptide synthesizer (Aaptec, Louisville, Ky.) using a split/mix method, and couplings were done using standard Fmoc SPPS chemistry in N-methylpyrrolidone (NMP).

Example 4

Screening Against 3D6

A21 with 3D6: Screening against 3D6 was carried out in four main steps:

Step 1 Preclear: 400 mg of OBOC library was blocked in 5% w/v dry milk in Tris buffered saline (TBS) (25 mM Tris-HCl, 150 mM NaCl, 10 mM $MgCl_2$, pH 7.6) for 2 hr at room temperature, and then incubated with 1:10,000 phosphatase-conjugated streptavidin (SA-AP, Promega, Madison, Wis.) in 0.5% w/v dry milk in TBS for 1 hr. The beads were washed in high salt buffer (25 mM Tris-HCl, 750 mM NaCl, 10 mM $MgCl_2$, pH 7.6) for 1 hr, and then developed with BCIP/NBT (Promega, Madison, Wis.) in BCIP buffer (100 mM Tris-HCl, 150 mM NaCl, 1 mM $MgCl_2$, pH 9). After 20 minutes, the reaction was quenched with conc. HCl, and the purple beads were discarded. The remaining library was decolorized in NMP, dried with methanol (MeOH) and dichloromethane (DCM), and then swelled and blocked in 5% w/v dry milk in TBS for 2 hr at room temperature.

Step 2 Target Screen: 4 mL of a solution containing 11.4 μM A21 and 147 nM 3D6 in 0.5% w/v dry milk in TBS was added to the precleared OBOC library, and the in situ click reaction was allowed to proceed overnight at 4° C. Bound target was probed with 1:10,000 AP-conjugated rabbit anti-human IgG Fc (Thermo Scientific, Rockford, Ill.) in 0.5% w/v dry milk in TBS for 1 hr at room temperature. The beads were then washed in high salt buffer for 1 hr at room temperature, and developed with BCIP/NBT in BCIP buffer. The reaction was quenched after 20 minutes with conc. HCl, and the purple beads were retained and decolorized in NMP and dried with MeOH and DCM. The hit beads were then stripped of all bound protein by washing with 7.5 M Guanidine-HCl (pH 2) for 2 hr at room temperature, rinsed 10 times with water, and then blocked in 5% w/v dry milk in TBS for 2 hr at room temperature.

Step 3 Anti-screen: A solution of 1% v/v human serum (Omega Scientific, Tarzana, Calif.) in TBS was incubated with the hit beads from Step 2 for 1 hr at room temperature. Off-target human antibodies bound to the beads were probed with 1:10,000 AP-conjugated rabbit anti-human IgG Fc in 0.5% w/v dry milk in TBS for 1 hr at room temperature. The beads were then washed in high salt buffer for 1 hr, and developed with BCIP/NBT in BCIP buffer. The reaction was quenched after 20 minutes with conc. HCl, and the purple beads were discarded. The remaining beads were decolorized in NMP and dried with MeOH and DCM. The anti-screened beads were swelled in water and washed with Guanidine-HCl for 2 hr at room temperature, rinsed 10 times with water, and then blocked in 5% w/v dry milk in TBS for 2 hr at room temperature.

Step 4 Product Screen: The beads were incubated for 1 hr at room temperature with 1:10,000 SA-AP in 0.5% w/v dry milk in TBS, washed for 1 hr with high salt buffer, and then developed with BCIP/NBT in BCIP buffer for 20 minutes. The reaction was quenched with conc. HCl, and the purple beads were retained and sequenced using a Procise Protein Sequencing System (Applied Biosystems, Kingston, R.I.).

Example 5

Screening Against 4B3

A22 with 4B3: Screening against 4B3 was carried out similarly to that described for 3D6, with two exceptions. In Step 2, the in situ click reaction solution contained 10 μM A22 and 430 nM 4B3 in 0.5% w/v dry milk in TBS. In Step 3, the beads were anti-screened against 0.1% v/v human serum in TBS spiked with 430 nM 3D6.

Example 6

Biligand Synthesis

Pra-OtBu: The C-terminally protected Pra molecule used in the synthesis of (i) and (ii) was made by refluxing Fmoc-L-Pra-OH (Aaptec, Louisville, Ky.) with tert-butyl-tricholroacetamide (Sigma-Aldrich, St. Louis, Mo.) at 50° C. for 3 hr in DCM. The formed product was separated from unreacted species on a silica flash column in DCM.

Peptides (i) and (ii): The secondary ligands including N-terminal $Az_4$ for (i) and (ii) were synthesized C→N on 200-300 mgs of Rink amide resin with a Titan peptide synthesizer using standard Fmoc chemistry. The synthesis used Fmoc and side chain protected D amino acids and L-$Az_4$ (Aaptec, Louisville, Ky.). Fmoc- and C-terminally protected Pra (Pra-OtBu) was clicked on-bead to the azide side chain of $Az_4$ by adding equal molar amounts of Pra-OtBu, Cu(I) iodide (Sigma-Aldrich, St. Louis, Mo.), and L-ascorbic acid (Sigma-Aldrich, St. Louis, Mo.), in 2× excess to the azide on bead. The click mixture was agitated in 20% v/v piperidine in NMP for 3 hr at room temperature, and the copper was chelated by repeated washing with 10% w/v sodium diethylduthiocarbamate trihydrate (Sigma-Aldrich, St. Louis, Mo.) and 10% v/v N,N-diisopropylethylamine (DIEA) (Sigma-Aldrich, St. Louis, Mo.) in NMP until the beads were clear. The Fmoc deprotected Pra was then the starting point for the remainder of the anchor component of each ligand, including N-terminal $PEG_5$ and biotin. The anchor components were synthesized using standard Fmoc chemistry with protected L amino acids. The finished peptides were side-chain deprotected and cleaved from resin in 95:5:5 TFA:$dH_2O$:TES, then precipitated in diethyl either. The ligands were cyclized by stirring the cleaved peptides dissolved in ~5 mL ACN overnight with 1 mL of the $Cu(phen)_3$ stock solution. The cyclization mixtures were lyophilized, and the final peptide products were purified using RP-HPLC. MALDI-TOF MS: (i): Expected mass $[M+H]^+$=2733.30, Observed mass $[M+H]^+$=2733.64. (ii): Expected mass $[M+H]^+$=2843.40, Observed mass $[M+H]^+$=2843.60.

Peptide (iii): A22 was synthesized, cyclized, and purified as described above. The secondary ligand component including N-terminal $Az_4$ for (iii) was synthesized C→N on Rink amide resin with a Titan peptide synthesizer using standard Fmoc chemistry. The synthesis used Fmoc and side chain protected D amino acids and L-$Az_4$. Resulting secondary peptide was side-chain deprotected and cleaved from resin in 95:5:5 TFA:$dH_2O$:TES, precipitated in diethyl either, and purified using RP-HPLC. The purified secondary peptide was clicked to A22 in solution by mixing with 2× molar excess of A22, 10×Cu(I) iodide, 50×L-ascorbic acid, and 4× Tris[(1-benzyl-1H-1,2,3-triazol-4-yl)methyl]amine (TBTA) (Sigma-Aldrich, St. Louis, Mo.) in 5:1 NMP:$dH_2O$ and stirring overnight at room temperature. The clicked biligand product was purified from the reaction mixture by RP-HPLC. Expected mass $[M+H]^+$=2720.31, Observed mass $[M+H]^+$=2720.5.

Scaling up (iii): The secondary ligands including N-terminally Boc-protected $Az_4$ for (iii) was synthesized C→N on Rink amide resin with a Titan peptide synthesizer using standard Fmoc chemistry. The synthesis used Fmoc and side chain protected D amino acids and L-$Az_4$ (AnaSpec, Fremont, CA). Truncated A22 (Pra-ICTTA(SEQ ID NO: 5)) was synthesized C→N on Sieber amide resin (ChemPep, Wellington, FL) with a Liberty 1 microwave peptide synthesizer (CEM, Matthews, NC) using standard Fmoc chemistry. The synthesis used Fmoc and side chain protected L amino acids and Fmoc-L-Pra. Fully protected truncated A22 was cleaved from the resin with 1% v/v TFA in DCM, and neutralized with DIEA. Solvent was removed using a rotary vacuum evaporator and the protected peptide was purified by RP-HPLC. Resulting truncated A22 was clicked on-bead to the secondary peptide through the azide side chain of Boc-$Az_4$ by adding equal molar amount of the protected truncated A22, 2× molar excess of Cu(I) iodide, and 2× excess of L-ascorbic acid to the azide on bead. The click mixture was agitated in 20% v/v piperidine in NMP overnight at room temperature, and then the copper was chelated by repeated washing with 10% w/v sodium diethylduthiocarbamate trihydrate and 10% v/v DIEA in NMP until the beads were clear. The Fmoc deprotected Pra was then the starting point for the remainder of the anchor component, including N-terminal $PEG_5$ and biotin (Biotin $PEG_5$ IWCGSGK (SEQ ID NO:27)). The anchor components were synthesized using standard Fmoc chemistry with protected L amino acids. The finished peptide was N-terminal and side-chain deprotected and cleaved from resin in 95:5:5 TFA:$dH_2O$:TES, then precipitated in diethyl either. The ligand was cyclized by stirring the cleaved peptide dissolved in ~5 mL ACN overnight with 1 mL of the $Cu(phen)_3$ stock solution. The cyclization mixtures were lyophilized, and the final peptide products were purified using RP-HPLC.

Example 7

Anchor Binding ELISA

Biotinylated anchor peptide was immobilized on streptavidin-coated 96-well plates (Thermo Scientific Pierce, Rockford, Ill.) at a concentration of 100 nM in TBS. The plates were blocked with 5% w/v dry milk in TBS, and then the anchor peptides were incubated with either 100 nM 3D6 or 4B3 in 0.5% w/v dry milk in TBS at room temperature for 1 hr. Bound antibody was probed with horseradish peroxidase (HRP)-conjugated mouse monoclonal antibody to human IgG Fc (Abcam, Cambridge, Mass.), diluted 1:10,000 in 0.5% w/v dry milk in TBS for 1 hr at room temperature. The colorimetric assay was developed with TMB substrate (KPL, Gaithersburg, Md.), then quenched with 1 M $H_2SO_4$ and read at 450 nm.

Example 8

Surface Plasmon Resonance

SPR experiments were performed on a Biacore T200 instrument. Biotinylated peptides were immobilized on streptavidin-coated sensor chips (GE Healthcare Biosciences, Pittsburgh, Pa.) at R.U. values ranging from 7-12. 4B3 or 3D6 was flowed at various concentrations in 1×HBS-EP buffer (GE Healthcare Biosciences, Pittsburgh, Pa.), and affinity curves were fit using the default settings of the Biacore evaluation software.

Example 9

Cocktail Binding ELISA

Recombinant multi-epitope chimeric HIV antigen ("chimera") (BioLink International, Lisle, Ill.) was chemically biotinylated using ChromaLink Biotin Labeling Kit (Solulink, San Diego, Calif.) according to the manufacturer's instructions, using 10× molar excess of the ChromaLink biotinylation reagent to the buffer-exchanged protein. Streptavidin-coated 96-well plates were saturated with the biotinylated biligand cocktail or chimera using 1 uM solutions in TBS. The plates were blocked with 5% w/v dry milk in TBS, and then the capture reagents were incubated with either 1% v/v human serum or a mixture of 4 nM each 3D6 and 4B3 spiked in 1% v/v human serum in TBS at room temperature for 1 hr. Bound antibody was probed with HPR-conjugated mouse monoclonal antibody to human IgG Fc, diluted 1:15,000 in 0.5% w/v dry milk in TBS for 1 hr at room temperature. The colorimetric assay was developed with TMB substrate, then quenched with 1 M $H_2SO_4$ and read at 450 nm (A450). The A450 for each sample is normalized against the A450 for the serum control, to yield a measurement of the signal-to-noise ratio of the assay.

Example 10

Patient Serum ELISA

Peripheral blood was obtained from HIV-1 infected patients at the University of California, Los Angeles (UCLA) Medical Center between July and August of 2012. Sera were stored at −80° C. before subsequent analysis. Streptavidin-coated 96-well plates were saturated with the biotinylated biligand cocktail or chimera using 1 uM solutions in TBS. The plates were blocked with 5% w/v dry milk in TBS, and then the capture reagents were incubated with patient serum samples diluted to 1% v/v in TBS containing 0.1% w/v bovine serum albumin (BSA). Additionally, both cocktail and chimera capture reagents were incubated with 1% v/v commercial healthy human serum in TBS. Bound antibody was probed with HRP-conjugated mouse monoclonal antibody to human IgG Fc, diluted 1:10,000 in TBS with 0.1% w/v BSA. The colorimetric assay was developed with TMB substrate, then quenched with 1 M $H_2SO_4$ and read at 450 nm (A450). The A450 for each sample is normalized against the A450 for the healthy control, to yield a measurement of the signal-to-noise ratio of the assay.

Example 11

Stability Assay

Small amounts of (iii) were stored under $N_2$ at 25° C., 37° C., or 57° C. for 58 days. Samples were diluted in 1:1 ACN/$H_2O$ with 0.1% v/v TFA to an equal concentration determined by measuring the absorbance values at 280 nm using NanoDropspectrophotometer (Thermo Scientific, Waltham, Mass.) and resolved by analytical RP-HPLC. The remaining samples were lyophilized and used in a single point sandwich ELISA. Streptavidin-coated 96-well plates were saturated with the samples of (iii) recovered from the storage experiments using 1 uM solutions in TBS. The plates were blocked with 5% w/v dry milk in TBS, then incubated with either 1% v/v human serum or 10 nM 4B3 spiked in 1% v/v human serum in 0.5% w/v dry milk in TBS at room temperature for 1 hr. Bound antibody was probed with HPR-conjugated mouse monoclonal antibody to human IgG Fc diluted 1:15,000 in 0.5% w/v dry milk in TBS. The colorimetric assay was developed with TMB substrate, then quenched with 1 M $H_2SO_4$ and read at 450 nm.

What is claimed is:

1. A synthetic capture agent produced by steps comprising (a) providing:

(i) an antibody of interest, wherein the antibody of interest is specific for an epitope, (ii) a compound comprising a peptide corresponding to the epitope and an azido group or an alkynyl group, and (iii) a library of candidate peptides, wherein the candidate peptides each comprise an amino acid sequence comprising the formula $X_1$-$X_2$-$X_3$-$X_4$-$X_5$, wherein $X_1$, $X_2$, $X_3$, $X_4$ and $X_5$, each represent glycine or a D-amino acid other than cysteine and methionine, wherein the candidate peptides each further comprise an azido group if the compound comprises an alkynyl group or an alkynyl group if the compound comprises an azido group; and (b) contacting the antibody of interest, the compound, and the library of candidate peptides, whereby a disubstituted 1,2,3-triazole linkage is formed between the compound and one of the candidate peptides when the azido group and alkynyl group of the compound and one of the candidate peptides are brought in close proximity upon binding to the antibody of interest, whereby the candidate peptide linked to the compound is identified as the candidate peptide to be used in the capture agent, wherein:

(i) the capture agent is the linked candidate peptide and compound formed in step (b) or (ii) the capture agent is formed by covalently linking together a separate instance of the peptide of the compound and a separate instance of the candidate peptide identified in step (b), thereby producing the capture agent, wherein the peptide of the compound and identified candidate peptide are linked together via a 1,4-substituted-1,2,3-triazole residue (Tz4) or via a 1,5-substituted-1,2,3-triazole residue (Tz5), wherein the capture agent specifically binds the antibody of interest.

2. The capture agent of claim 1, wherein the capture agent is labeled with a label selected from the group consisting of biotin, copper-DOTA, biotin-PEG3, aminooxyacetate, $^{19}$FB, $^{18}$FB and FITC-PEG3.

3. The capture agent of claim 1, wherein the capture agent is labeled with the detectable moiety selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br.

4. A synthetic capture agent, wherein the capture agent specifically binds an anti-gp41 antibody, wherein the capture agent has the structure:

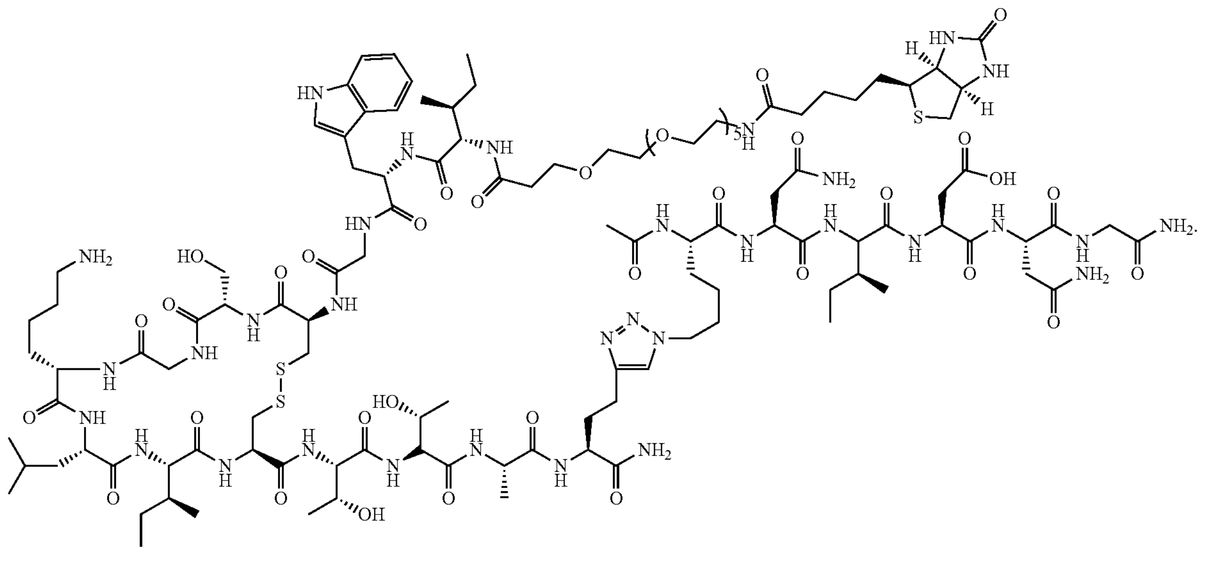

5. A composition comprising two or more capture agents of claim 1.

6. The synthetic capture agent of claim 1, wherein the antibody of interest is an anti-gp41 antibody, wherein the peptide of the compound comprises the amino acid sequence of IWCGSGKLICTTA (SEQ ID NO: 1), wherein the identified candidate peptide comprises the amino acid sequence selected from the group consisting of dkGlp (SEQ ID NO: 8); vadpa (SEQ ID NO: 9); nidnG (SEQ ID NO: 2); pGvtf (SEQ ID NO: 10); srrrs (SEQ ID NO: 11); dq/eGaf (SEQ ID NO: 12); ywdyn (SEQ ID NO: 13); hllyq (SEQ ID NO: 14); sGaqs (SEQ ID NO: 15); ddwai (SEQ ID NO: 16); qidlr (SEQ ID NO: 17); tfLqs (SEQ ID NO: 18); hnpfk (SEQ ID NO: 3); wGehp (SEQ ID NO: 19); qndwK (SEQ ID NO: 20); ItsrY (SEQ ID NO: 21); diksp (SEQ ID NO: 22); eihny (SEQ ID NO: 4); qpidq (SEQ ID NO: 23); kidrv (SEQ ID NO: 24); qsp/dwl (SEQ ID NO: 25); and eqtfd (SEQ ID NO: 26).

7. The capture agent of claim 1, wherein the antibody of interest is an anti-gp41 antibody.

8. The synthetic capture agent of claim 1, wherein the capture agent specifically binds an anti-gp41 antibody, wherein the peptide of the compound comprises an amino acid sequence 80 to 100% identical to IWCGSGKLICTTA (SEQ ID NO: 1), wherein the identified candidate peptide comprises an amino acid sequence 80 to 100% identical to an amino acid sequence selected from the group consisting of dkGlp (SEQ ID NO: 8); vadpa (SEQ ID NO: 9); nidnG (SEQ ID NO: 2); pGvtf (SEQ ID NO: 10); srrrs (SEQ ID NO: 11); dq/eGaf (SEQ ID NO: 12); ywdyn (SEQ ID NO: 13); hllyq (SEQ ID NO: 14); sGaqs (SEQ ID NO: 15); ddwai (SEQ ID NO: 16); qidlr (SEQ ID NO: 17); tfLqs (SEQ ID NO: 18); hnpfk (SEQ ID NO: 3); wGehp (SEQ ID NO: 19); qndwK (SEQ ID NO: 20); ItsrY (SEQ ID NO: 21); diksp (SEQ ID NO: 22); eihny (SEQ ID NO: 4); qpidq (SEQ ID NO: 23); kidrv (SEQ ID NO: 24); qsp/dwl (SEQ ID NO: 25); and eqtfd (SEQ ID NO: 26).

9. The synthetic capture agent of claim 1, wherein the peptide of the compound comprises the amino acid sequence IWCGSGKLICTTA (SEQ ID NO: 1), wherein the identified candidate peptide comprises an amino acid sequence selected from the group consisting of dkGlp (SEQ ID NO: 8); vadpa (SEQ ID NO: 9); nidnG (SEQ ID NO: 2); pGvtf (SEQ ID NO: 10); srrrs (SEQ ID NO: 11); dq/eGaf (SEQ ID NO: 12); ywdyn (SEQ ID NO: 13); hllyq (SEQ ID NO: 14); sGaqs (SEQ ID NO: 15); ddwai (SEQ ID NO: 16); qidlr (SEQ ID NO: 17); tfLqs (SEQ ID NO: 18); hnpfk (SEQ ID NO: 3); wGehp (SEQ ID NO: 19); qndwK (SEQ ID NO: 20); ItsrY (SEQ ID NO: 21); diksp (SEQ ID NO: 22); eihny (SEQ ID NO: 4); qpidq (SEQ ID NO: 23); kidrv (SEQ ID NO: 24); qsp/dwl (SEQ ID NO: 25); and eqtfd (SEQ ID NO: 26).

10. The capture agent of claim 9, wherein the identified candidate peptide comprises an amino acid sequence selected from the group consisting of nidnG (SEQ ID NO: 2), hnpfk (SEQ ID NO: 3) and eihny (SEQ ID NO: 4).

11. The capture agent of claim 10, wherein the identified candidate peptide comprises the amino acid sequence nidnG (SEQ ID NO: 2).

12. The capture agent of claim 10, wherein the identified candidate peptide comprises the amino acid sequence hnpfk (SEQ ID NO: 3).

13. The capture agent of claim 10, wherein the identified candidate peptide comprises the amino acid sequence eihny (SEQ ID NO: 4).

14. The capture agent of claim 8, wherein the capture agent is labeled with a label selected from the group consisting of biotin, copper-DOTA, biotin-PEG3, aminooxyacetate, $^{19}$FB, $^{18}$FB and FITC-PEG3.

15. The capture agent of claim 8, wherein the capture agent is labeled with the detectable moiety selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br.

16. The capture agent of claim 7, wherein the peptide of the compound comprises an amino acid sequence 80 to 100% identical to IWCGSGKLICTTA (SEQ ID NO: 1).

17. The capture agent of claim 16, wherein the identified candidate peptide comprises an amino acid sequence 80 to 100% identical to an amino acid sequence selected from the group consisting of dkGlp (SEQ ID NO: 8); vadpa (SEQ ID NO: 9); nidnG (SEQ ID NO: 2); pGvtf (SEQ ID NO: 10); srrrs (SEQ ID NO: 11); dq/eGaf (SEQ ID NO: 12); ywdyn (SEQ ID NO: 13); hllyq (SEQ ID NO: 14); sGaqs (SEQ ID NO: 15); ddwai (SEQ ID NO: 16); qidlr (SEQ ID NO: 17); tfLqs (SEQ ID NO: 18); hnpfk (SEQ ID NO: 3); wGehp (SEQ ID NO: 19); qndwK (SEQ ID NO: 20); ItsrY (SEQ ID NO: 21); diksp (SEQ ID NO: 22); eihny (SEQ ID NO: 4); qpidq (SEQ ID NO: 23); kidrv (SEQ ID NO: 24); qsp/dwl (SEQ ID NO: 25); and eqtfd (SEQ ID NO: 26).

18. The capture agent of claim 6, wherein the identified candidate peptide comprises an amino acid sequence selected from the group consisting of nidnG (SEQ ID NO: 2), hnpfk (SEQ ID NO: 3) and eihny (SEQ ID NO: 4).

19. The capture agent of claim 18, wherein the identified candidate peptide comprises the amino acid sequence of nidnG (SEQ ID NO: 2).

20. The capture agent of claim 18, wherein the identified candidate peptide comprises an amino acid sequence of hnpfk (SEQ ID NO: 3).

21. The capture agent of claim 18, wherein the identified candidate peptide comprises an amino acid sequence of eihny (SEQ ID NO: 4).

22. The capture agent of claim 8 having the structure:

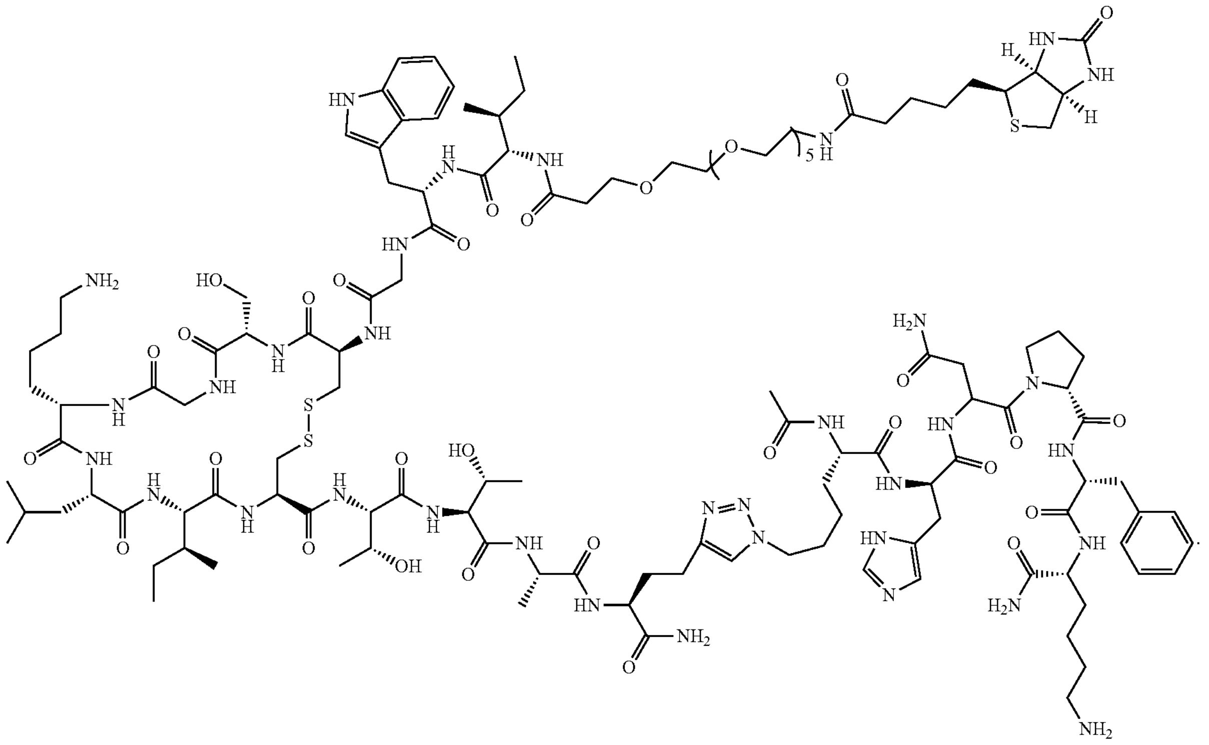

23. The capture agent of claim 8 having the structure:

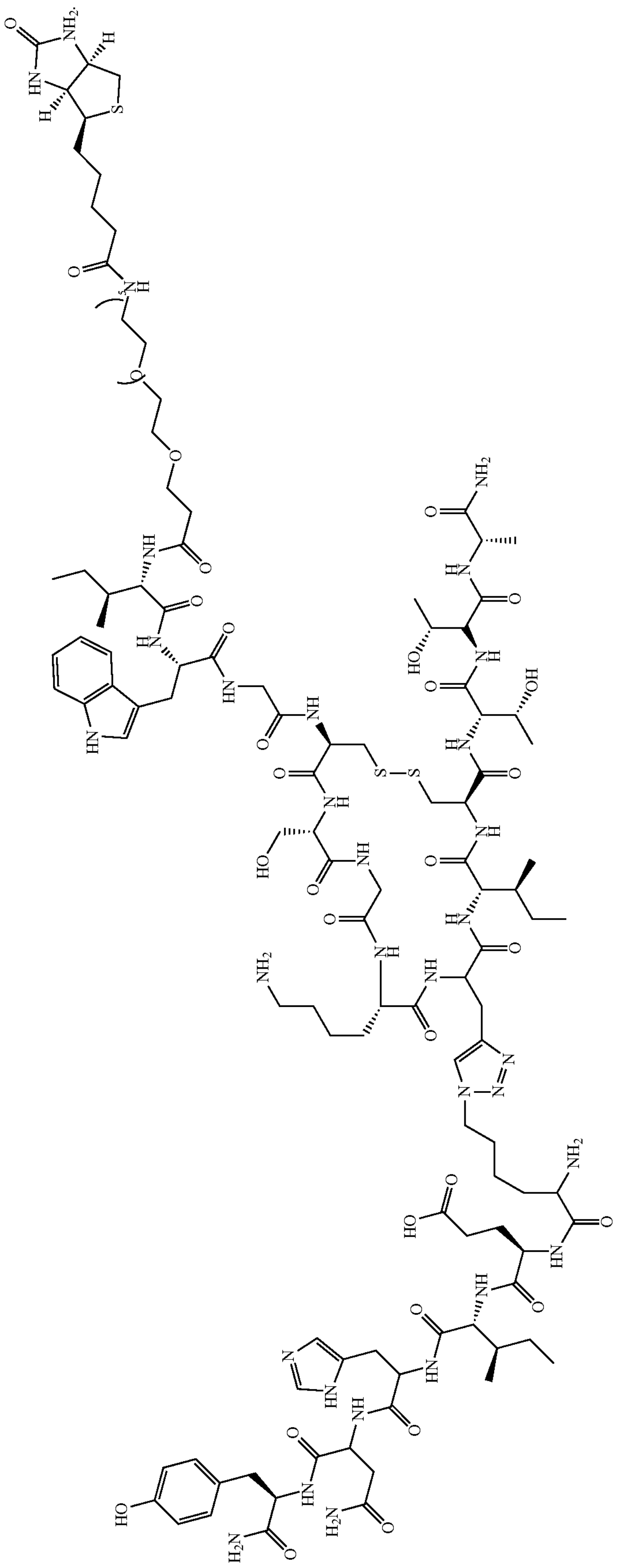

24. A multiplex capture agent comprising two or more capture agents of claim 7, wherein the two or more capture agents are covalently linked together, wherein the multiplex capture agent specifically binds two or more anti-gp41 antibodies.

25. The capture agent of claim 7, wherein the peptide of the compound comprises an epitope of gp41.

26. The capture agent of claim 16, wherein the peptide of the compound comprises the amino acid sequence of IWCGSGKLICTTA (SEQ ID NO: 1).

* * * * *